United States Patent [19]
Wright et al.

[11] Patent Number: 5,928,152
[45] Date of Patent: Jul. 27, 1999

[54] METHOD AND APPARATUS FOR A BASEBAND PROCESSOR OF A RECEIVE BEAMFORMER SYSTEM

[75] Inventors: J. Nelson Wright, Menlo Park; Christopher R. Cole, Cupertino; Albert Gee, Los Altos, all of Calif.

[73] Assignee: Acuson Corporation, Mountain View, Calif.

[21] Appl. No.: 08/434,160

[22] Filed: May 2, 1995

Related U.S. Application Data

[63] Continuation-in-part of application No. 08/286,658, Aug. 5, 1994, abandoned, and application No. 08/419,595, Apr. 7, 1995, Pat. No. 5,623,928, which is a continuation of application No. 08/286,510, Aug. 5, 1994, abandoned.

[51] Int. Cl.[6] ........................................................ A61B 8/00
[52] U.S. Cl. ............................................................ 600/447
[58] Field of Search .................................... 600/443, 447; 73/625, 626; 367/7, 11

[56] References Cited

U.S. PATENT DOCUMENTS

| | | | |
|---|---|---|---|
| 3,805,596 | 4/1974 | Klahr | 73/67.8 |
| 4,140,022 | 2/1979 | Maslak | 73/626 |
| 4,154,113 | 5/1979 | Engeler | 73/626 |
| 4,155,258 | 5/1979 | Engeler et al. | 73/626 |
| 4,155,259 | 5/1979 | Engeler | 73/626 |
| 4,155,260 | 5/1979 | Engeler et al. | 73/626 |
| 4,180,790 | 12/1979 | Thomas | 367/7 |
| 4,191,957 | 3/1980 | Walker et al. | 343/5 PC |
| 4,241,412 | 12/1980 | Swain . | |
| 4,254,662 | 3/1981 | Kuroda et al. . | |
| 4,368,643 | 1/1983 | Tachita et al. . | |
| 4,468,747 | 8/1984 | Leavitt et al. . | |
| 4,471,449 | 9/1984 | Leavitt et al. . | |
| 4,484,477 | 11/1984 | Buxton | 73/626 |
| 4,550,607 | 11/1985 | Maslak et al. | 73/626 |
| 4,662,223 | 5/1987 | Riley et al. | 73/626 |
| 4,669,314 | 6/1987 | Magrane | 73/610 |

(List continued on next page.)

FOREIGN PATENT DOCUMENTS

| | | |
|---|---|---|
| 0473 959 A2 | of 0000 | European Pat. Off. . |
| 0484181 A1 | of 0000 | European Pat. Off. . |
| 545 788 A1 | 11/1992 | European Pat. Off. . |
| 2112 937 | of 0000 | United Kingdom . |
| WO 93/12/444 | 6/1993 | WIPO . |

OTHER PUBLICATIONS

Beamforming, Dan E. Dudgeon & Russell M. Mersereau, *Multidimensional Digital Signal Processing*, Section 6.2, Prentice Hall, 1984.

Digital Signal Processing for Sonar, William C. Knight, Roger G. Pridham, Steven M. Kay, *Proceedings of the IEEE*, vol. 69, No. 11, Nov., 1981.

(List continued on next page.)

*Primary Examiner*—Francis J. Jaworski
*Attorney, Agent, or Firm*—Brinks Hofer Gilson & Lione

[57] ABSTRACT

This invention presents a multi-beam baseband processor for making post-beamformation adjustments to the complex (in-phase/quadrature) pre-detection scan line samples acquired from a receive beamformer of an ultrasound imaging system. Specifically, the invention includes a programmable finite impulse response (FIR) filter and a programmable complex multiplier. The programmable filter performs signal shaping and sample-rate conversion. The signal shaping capability may be used to compensate for transducer and analog signal path responses, to increase signal-to-noise ratio (SNR) by rejecting out-of-band noise frequencies, to operate as a matched filter to the transmitted waveform shape, and to act as both a smoothing and anti-aliasing filter during rate-conversion operation. The programmable multiplier permits both amplitude and phase adjustments of the complex data that assures amplitude and phase coherency between acquired scan lines, compensating for the effects of a selected scan format or the differences in ultrasound frequencies used to produce each scan line.

59 Claims, 10 Drawing Sheets

Microfiche Appendix Included
(195 Microfiche, 19058 Pages)

U.S. PATENT DOCUMENTS

| | | |
|---|---|---|
| 4,691,570 | 9/1987 | Hassler ................................... 73/626 |
| 4,699,009 | 10/1987 | Maslah et al. ........................... 73/626 |
| 4,733,562 | 3/1988 | Saugeon .................................. 73/626 |
| 4,787,392 | 11/1988 | Saugeon .................................. 73/625 |
| 4,809,184 | 2/1989 | O'Donnell et al. ............... 364/413.25 |
| 4,817,617 | 4/1989 | Takeuchi et al. . |
| 4,829,491 | 5/1989 | Saugeon et al. ........................ 367/103 |
| 4,831,601 | 5/1989 | Breimesser et al. ..................... 367/88 |
| 4,839,652 | 6/1989 | O'Donnell et al. ..................... 341/122 |
| 4,852,577 | 8/1989 | Smith et al. ............................ 600/443 |
| 4,886,069 | 12/1989 | O'Donnell ............................. 128/661 |
| 4,893,284 | 1/1990 | Magrane .................................. 367/12 |
| 4,896,287 | 1/1990 | O'Donnell et al. ..................... 364/754 |
| 4,974,558 | 12/1990 | Katakura et al. ......................... 73/626 |
| 4,975,885 | 12/1990 | Hassler et al. ............................. 367/7 |
| 4,983,970 | 1/1991 | O'Donnell et al. ..................... 341/122 |
| 5,005,419 | 4/1991 | O'Donnell et al. ....................... 73/626 |
| 5,014,710 | 5/1991 | Maslak et al. ...................... 128/660.05 |
| 5,014,712 | 5/1991 | O'Donnell et al. ................ 128/661.01 |
| 5,027,821 | 7/1991 | Hirama et al. . |
| 5,047,769 | 9/1991 | Engeler et al. ......................... 341/118 |
| 5,047,770 | 9/1991 | Engeler et al. ......................... 341/120 |
| 5,105,814 | 4/1992 | Drukarev et al. ....................... 128/660 |
| 5,111,695 | 5/1992 | Engeler et al. ........................... 73/626 |
| 5,121,364 | 6/1992 | O'Donnell .............................. 367/98 |
| 5,127,409 | 7/1992 | Daigle . |
| 5,128,903 | 7/1992 | Hassler et al. .......................... 367/103 |
| 5,140,558 | 8/1992 | Harrison, Jr. et al. ..................... 367/11 |
| 5,142,649 | 8/1992 | O'Donnell ................................. 367/7 |
| 5,165,413 | 11/1992 | Maslak et al. ...................... 128/660.05 |
| 5,197,037 | 3/1993 | Leavitt .................................... 367/11 |
| 5,203,335 | 4/1993 | Noujaim et al. ................... 128/660.01 |
| 5,218,869 | 6/1993 | Hummer .................................. 73/629 |
| 5,228,007 | 7/1993 | Murakami et al. ..................... 367/103 |
| 5,230,340 | 7/1993 | Rhyne ................................ 128/661.01 |
| 5,231,573 | 7/1993 | Takanizawa ...................... 364/413.25 |
| 5,235,982 | 8/1993 | O'Donnell et al. ..................... 660/443 |
| 5,249,578 | 10/1993 | Karp et al. .......................... 128/661.01 |
| 5,268,876 | 12/1993 | Rachlin . |
| 5,276,654 | 1/1994 | Mallart et al. ............................. 367/7 |
| 5,278,757 | 1/1994 | Hoctor et al. . |
| 5,295,118 | 3/1994 | Gilmour . |
| 5,301,674 | 4/1994 | Erikson et al. ..................... 128/661.01 |
| 5,318,033 | 6/1994 | Savord ............................... 128/661.01 |
| 5,329,930 | 7/1994 | Thomas, III ....................... 128/661.01 |
| 5,331,964 | 7/1994 | Trohey et al. .......................... 600/447 |
| 5,345,426 | 9/1994 | Lipschutz ............................... 367/123 |
| 5,390,674 | 2/1995 | Robinson et al. . |
| 5,431,167 | 7/1995 | Savord . |
| 5,462,057 | 10/1995 | Hunt et al. . |
| 5,488,588 | 1/1996 | Engeler et al. ............................ 367/7 |
| 5,566,675 | 10/1996 | Li et al. .................................. 600/447 |

OTHER PUBLICATIONS

Digital Time Delay Beamforming, Roger Pridham, *Signal Processing Handbook*, edited by C.H. Chen, 1988.

Fundamentals of Digital Array Processing, Dan E. Dudgeon, *Proceedings of the IEEE*, vol. 65, No. 6, Jun. 1977.

The Development of an Ultrasound Diagnostic System with the Ability of Parallel Signal Receiving Using Digital Beam Formers, Hirama, et al., Article 63V–1, Japan Medical Ultrasound Conference, Nov. 1993.

Digital Beamforming Antennas; An Introduction, Hans Steyskal *Microwave Journal*, Jan. 1987.

Acoustic Imaging for Nondestructive Evaluation, Gordon S. Kino, *Proceedings of the IEEE*, vol. 67, pp. 510–525, Apr., 1979.

Acuson 128 Computer Sonography Systems Service Manual, pp. 13–32, 113–115, Acuson Corp. Aug. 1989.

Underwater Acoustic Imaging, Jerry L. Sutton, *Proceedings of the IEEE*, vol. 67, pp. 554–556, Apr., 1979.

Digital Beamforming for Radar, P. Barton, *Proceedings of the IEEE*, vol. 127, pt. F, No. 4, Aug. 1980.

A Digital Synthetic Focus Acoustic Imaging System, P.D. Carl, G.S. Kino, C.S. Desilets, and P.M. Grant, *Acoustic Imaging*, vol. 8, 1978.

Digital Beamforming in Ultrasound, B.D. Steinberg, *IEEE Transactions of Ultrasonics, Ferroelectronics, and Frequency Control*, vol. 39, Nov. 1992.

Multirate Digital Signal Processing, Ronald E. Crochiere and Lawrence R. Rabiner, Prentice–Hall, 1983.

Digital Signal Processing Applications Using the ADSP–2100 Family, vol. 1, Amy Mar, ed., Prentice–Hall, 1992.

A Novel Approach to Digital Beamforming, Roger Pridham and Ronald A. Mucci, *Journal of the Acoustical Society of America*, vol. 63, Feb. 1978.

Digital Interpolation Beamforming for Low Pass and Band Pass Signals, Roger G. Pridham and Ronald A. Mucci, *Proceedings of the IEEE*, vol. 67, Jun. 1979.

Beam Transformation Techniques for Ultrasonic Medical Imaging, Alex Drukarev, Konstantinoes Konstantinides, Gadiel Seroussi, *IEEE Transactions of Ultrasonics, Ferroelectrics, and Frequency Control*, vol. 40, No. 6, Nov. 1993.

A Comparison of Algorithms for Polar–to–Cartesian Interpolation in Spotlight Mode Star, David C. Munson, Jr., Jorge L. C. Sanz, W. Kenneth Jenkins, Gary Kakazu, and Bruce C. Mather, *ICASSP*, vol. 3, 1985.

Discrete Fast Algorithms for Two Dimensional Linear Prediction on a Polar Raster, Wen–Hsien Fang, Andrew E. Yagle, *IEEE Transactions of Signal Processing*, vol. 40, No. 6, Jun. 1992.

FFT Signal Processing and System Applications, E. Oran Brigham, Avantek, Inc., *The Fast Fourier Transform and Its Applications*.

High–Speed Ultrasound Volumetric Imaging System—Part I: Transducer Designand Beam Steering, Stephen W. Smith, Henry G. Pavy, Jr., and Olaf T. von Ramm, *IEEE Transactions on Ultrasonics, Ferroelectrics, and Frequency Control*, vol. 38, No. 2, Mar. 1991.

High–Speed Ultrasound Volumetric Imaging System—Part II: Parallel Processing and Image Display, Stephen W. Smith, Henry G. Pavy, Jr., and Olaf T. von Ramm, *IEEE Transactions on Ultrasonics, Ferroelectrics, and Frequency Control*, vol. 38, No. 2, Mar. 1991.

Nearest Neighbor and Generalized Inverse Distance Interpolation for Fourier Domain Image Reconstruction, W. Kenneth Jenkins, Bruce C. Mather, David C. Munson, Jr., *ICASSP*, vol. 3, 1985.

The Reconstruction of a Multidimensional Sequence from the Phase or Magnitude of Its Fourier Transform, Monson H. Hayes, *IEEE Transactions on Acoustics, Speech, and Signal Processing*, vol. 30, No. 2, Apr. 1992.

Sampling Continuous 2–D Signals, Dan E. Dudgeon, Russell M. Mersereau, *Multidimensional Digital Signal Processing*, Chapter 1, Section 1.4.

A Scan Conversion Algorithm for Displaying Ultrasound Images, Steven C. Leavitt, Barry F. Hunt, Hugh G. Larsen, *Hewlett–Packard Journal*, vol. 34, No. 10, Oct. 1983.

Support–Limited Extrapolation of Offset Fourier Data, David C. Munson, Jr. and Eric A. Ullman, *ICASSP*, vol. 4, 1986.

A Tomographic Formulation of Spotlight–Mode Synthetic Aperture Radar, David C. Munson, Jr., James Dennis O'Brien, W. Kenneth Jenkins, *Proceedings of the IEEE*, vol. 71, No. 8, Aug. 1983.

"Analysis of a Scan Conversion Algorithm for a Real–Time Sector Scanner" by Min Hwa Lee, Joo Han Kim and Song Bai Park.

"Weighted Least–Squares Pulse–Shaping Filters With Application to Ultrasonic Signals" by Bengt Mandersson and Goran Salomonsson.

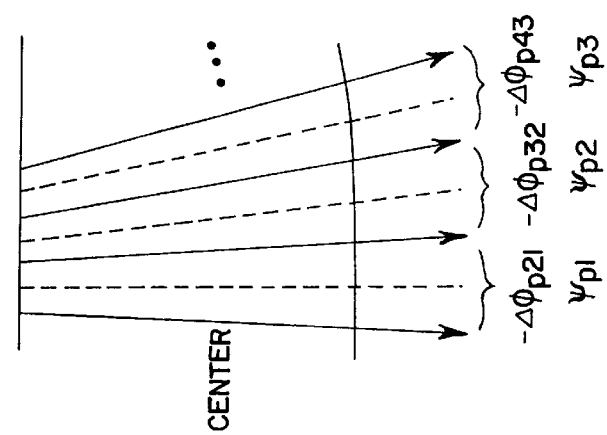
FIG. 8
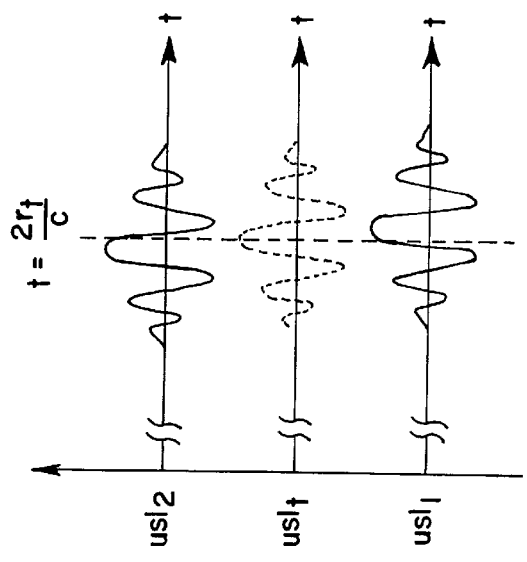
FIG. 7
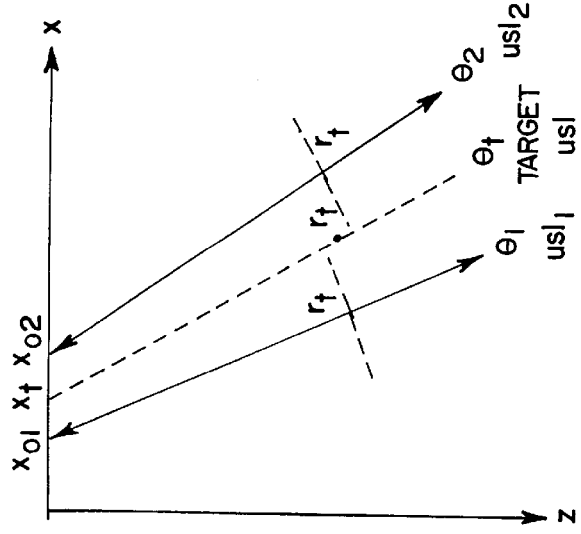

METHOD AND APPARATUS FOR A BASEBAND PROCESSOR OF A RECEIVE BEAMFORMER SYSTEM

REFERENCE TO RELATED APPLICATIONS

This application is a continuation in part of Ser. Nos. 08/286,658 entitled METHOD AND APPARATUS FOR RECEIVE BEAMFORMER SYSTEM, filed Aug. 5, 1994, J. Wright et al., abandoned and 08/419,595 entitled METHOD AND APPARATUS FOR COHERENT IMAGE FORMATION, filed Apr. 7, 1995, now U.S. Pat. No. 5,623,928, which is a continuation of Ser. No. 08/286,510, filed Aug. 5, 1994, now abandoned.

CROSS-REFERENCE TO RELATED APPLICATIONS

This application is related to:

a. METHOD AND APPARATUS FOR RECEIVE BEAMFORMER SYSTEM, J. Wright et al., Attorney Docket No. 5055-77;

b. METHOD AND APPARATUS FOR TRANSMIT BEAMFORMER SYSTEM, Cole et al., Attorney Docket No. 5055-78;

c. METHOD AND APPARATUS FOR FOCUS CONTROL OF TRANSMIT AND RECEIVE BEAMFORMER SYSTEMS, Gee et al., Attorney Docket No. 5055-79;

d. METHOD AND APPARATUS FOR DOPPLER RECEIVE BEAMFORMER SYSTEM, Maslak et al., Attorney Docket No. 5055-80;

e. METHOD AND APPARATUS FOR ADJUSTABLE FREQUENCY SCANNING IN ULTRASOUND IMAGING, Wright et al., Attorney Docket No. 5055-83;

f. METHOD AND APPARATUS FOR BEAMFORMER SYSTEM WITH VARIABLE APERTURE, Cole et al., Attorney Docket No. 5055-85.

The above related applications are all commonly assigned with the present application, filed concurrently with the present application, and are incorporated herein by reference in their entirety.

The present application is also related to the following previously filed applications:

a. METHOD AND APPARATUS FOR REAL-TIME, CONCURRENT ADAPTIVE FOCUSING IN AN ULTRASOUND BEAMFORMER IMAGING SYSTEM, Wright et al., Ser. No. 08/286,528, filed Aug. 5, 1994;

b. METHOD AND APPARATUS FOR A GEOMETRIC ABERRATION TRANSFORM IN AN ADAPTIVE FOCUSING ULTRASOUND BEAMFORMER SYSTEM, Wright et al., Ser. No. 08/286,664, filed Aug. 5, 1994.

REFERENCE TO MICROFICHE APPENDIX

This application includes a microfiche appendix of 195 sheets of microfiche having 19,058 frames. A portion of the disclosure of this patent document contains material which is subject to copyright protection. The copyright owner has no objection to the facsimile reproduction by any one of the patent disclosure, as it appears in the Patent and Trademark Office patent files or records, but otherwise reserves all copyright rights whatsoever.

BACKGROUND OF THE INVENTION

This invention relates to coherent imaging systems including, for example, radar, sonar, seismic, and ultrasound systems, using vibratory energy, and in particular, but not limited to, phased array ultrasound imaging systems for scan formats such as, by way of example only, linear, steered linear, sector, circular, Vector®, steered Vector® in imaging modes such as, by way of example only, B-mode (gray-scale) imaging mode and color Doppler imaging mode. In particular, this invention describes post-beamformation signal processing adjustments. Although the invention will be discussed with respect to an ultrasound system, the invention can be implemented with other types of coherent imaging systems.

Beam-to-beam coherency is not required in most prior art ultrasonic imaging systems, although the need for channel-to-channel coherency in phased array imaging systems is well understood. In prior art systems, a requirement for image uniformity is that the amplitude response of the system to a point target at any range on any scan line be substantially identical to the amplitude response to the same target at the same range on an adjacent scan line. The additional requirement for beam-to-beam coherency further implies the phase response (jointly represented with the amplitude response by, for example, an in-phase and quadrature (I/Q) response) of the system to a point target at any range on any scan line also to be substantially identical to the phase response to the same target at the same range on an adjacent scan line. Systematic phase variations can arise in some scan formats. For example, if the apertures associated with successive transmit and receive beams change relative to each other, systematic scan-line-to-scan-line phase variations can be introduced. Likewise, systematic scan-line-to-scan-line phase variations can be introduced if the center frequencies of successive transmit and receive beams change relative to each other. This method requires range-dependent and scan-line-dependent phase correction or adjustments of such systematic variations. Such phase corrections or adjustments may be predetermined and stored in memory to be applied by a complex multiplier to the acquired coherent samples prior to further coherent operations, such as synthesizing new coherent samples as disclosed in co-pending patent application: METHOD AND APPARATUS FOR COHERENT IMAGE FORMATION which is incorporated herein by reference in its entirety.

As further discussed in co-pending U.S. Patent Application entitled METHOD AND APPARATUS FOR ADJUSTABLE FREQUENCY SCANNING IN ULTRASOUND IMAGING, it is also desirable to adjust for systematic phase variations to establish coherent phase alignment among pre-detected beams in a scan caused by differences in beam-to-beam transmit/receive frequencies by remodulating prior to detection. This is most efficiently performed on the beamformed baseband I/Q signals.

Ultrasound imaging is accomplished by firing (transmitting) into body tissue or other objects to be imaged a scan sequence of focused ultrasonic beams centered along straight lines in space called transmit scan lines. The transmit scan lines are generated by a transmit beamformer and an ultrasound transducer array. The transmit scan lines are spaced to produce a planar linear, planar sector or other display of the tissue via a pre-defined firing or scanning pattern. Focused to some defined depth in the tissue, the ultrasonic transmit continuous-wave (CW) or pulse-wave (PW) signal, propagating at an assumed constant propagation velocity of nominally c=1540 m/sec through the tissue, interacts with the tissue and reflects a small portion of the signal back to the ultrasound transducer array that initiated the ultrasound signal. The round trip delay time is shortest for those targets closest to the ultrasound transducer array, and longest for those targets farthest from the transducer array. With the application of appropriate time delays, the receive beamformer can dynamically focus receive beams along straight lines in space called receive scan lines commencing, for example, with the shallowest range (depth) of interest and evolving toward the deepest range of interest.

Analog and hybrid (analog-digital) phased array beamformer systems are available in the known art. For example, phase array beamformer systems can be found in the following patents which are incorporated herein by reference.

| U.S. Pat. No. : | Title: | Inventor(s): |
|---|---|---|
| 4,140,022 | MULTIPLE TRANSDUCER ACOUSTIC IMAGING APPARATUS | Samuel H. Maslak |
| 4,550,607 | PHASED ARRAY ACOUSTIC IMAGING SYSTEM | Samuel H. Maslak J. Nelson Wright |
| 4,699,009 | DYNAMICALLY FOCUSED LINEAR PHASED ARRAY ACOUSTIC IMAGING SYSTEM | Samuel H. Maslak Hugh G. Larsen |
| 5,014,710 and 5,165,413 | STEERED LINEAR COLOR DOPPLER IMAGING | Samuel H. Maslak Donald J. Burch J. Nelson Wright Donald R. Langdon Joel S. Chaffin Grant Flash, III |

Digital receive beamformer systems have also been proposed in the art with respect to ultrasound systems. By way of example, the following U.S. patents, discuss various aspects of such systems. The patents include:

| U.S. Pat. No. : | Title: | Inventor(s): |
|---|---|---|
| 4,809,184 | METHOD AND APPARATUS FOR FULLY DIGITAL BEAM FORMATION IN A PHASED ARRAY COHERENT IMAGING SYSTEM | Matthew O'Donnell Mark Magrane |
| 4,839,652 | METHOD AND APPARATUS FOR HIGH SPEED DIGITAL PHASED ARRAY COHERENT IMAGING SYSTEM | Matthew O'Donnell William E. Engeler Thomas L. Vogelsong Steven G. Karr Sharbel E. Noujaim |
| 4,886,069 | METHOD OF, AND APPARATUS FOR, OBTAINING A PLURALITY OF DIFFERENT RETURN ENERGY IMAGING BEAMS RESPONSIVE TO A SINGLE EXCITATION EVENT | Matthew O'Donnell |
| 4,893,284 | CALIBRATION OF PHASED ARRAY ULTRASOUND PROBE | Mark G. Magrane |
| 4,896,287 | CORDIC COMPLEX MULTIPLIER | Matthew O'Donnell William E. Engeler |
| 4,975,885 | DIGITAL INPUT STAGE FOR AN ULTRASOUND APPARATUS | Dietrich Hassler Erhard Schmidt Peter Wegener |
| 4,983,970 | METHOD AND APPARATUS FOR DIGITAL PHASED ARRAY IMAGING | Matthew O'Donnell William E. Engeler John J. Bloomer John T. Pedicone |
| 5,005,419 | METHOD AND | Matthew O'Donnell |

-continued

| U.S. Pat. No. : | Title: | Inventor(s): |
|---|---|---|
|  | APPARATUS FOR COHERENT IMAGING SYSTEM | Kenneth B. Welles, II Carl R. Crawford Norbert J. Plec Steven G. Karr |
| 5,111,695 | DYNAMIC PHASE FOCUS FOR COHERENT IMAGING BEAM FORMATION | William E. Engeler Matthew O'Donnell John T. Pedicone John J. Bloomer |
| 5,142,649 | ULTRASONIC IMAGING SYSTEM WITH MULTIPLE, DYNAMICALLY FOCUSED TRANSMIT BEAMS | Matthew O'Donnell |
| 5,230,340 | ULTRASOUND IMAGING SYSTEM WITH IMPROVED DYNAMIC FOCUSING | Theador L. Rhyne |
| 5,235,982 | DYNAMIC TRANSMIT FOCUSING OF A STEERED ULTRASONIC BEAM | Matthew O'Donnell |
| 5,249,578 | ULTRASOUND IMAGING SYSTEM USING FINITE IMPULSE RESPONSE DIGITAL CLUTTER FILTER WITH FORWARD AND REVERSE COEFFICIENTS | Sidney M. Karp Raymond A. Beaudin |

The basic feature of a digital receive beamformer system as disclosed above can include: (1) amplification of the ultrasound signal received at each element of an array such as, for example, a linear array; (2) direct per channel analog-to-digital conversion of the ultrasound signal with an analog-to-digital sampling rate at least twice the highest frequency in the signal; (3) a digital memory to provide delays for focusing; and (4) digital summation of the focused signals from all the channels. Other processing features of a receive beamformer system can include phase rotation of a receive signal on a channel-by-channel basis to provide fine focusing, amplitude scaling (apodization) to control the beam sidelobes, and digital filtering to control the bandwidth of the signal. This art points out the ever present desire to achieve, in an efficient manner, a reconstructed image of high quality.

SUMMARY OF THE INVENTION

The present invention relates to a method and apparatus which provides for a baseband processor for making post-beamformation adjustments to the complex (in-phase/quadrature) pre-detection scan line samples acquired from a receive beamformer of an ultrasound imaging system. A suitable digital receive beamformer is described, for example, in the referenced co-pending patent application entitled: METHOD AND APPARATUS FOR RECEIVE BEAMFORMER SYSTEM.

In a preferred embodiment, the invention includes a programmable finite impulse response (FIR) filter and a programmable complex multiplier. In one aspect of the invention, the programmable filter performs signal shaping. The signal shaping capability may be used to compensate for transducer and analog signal path responses that distort the transmitted and received ultrasound waveforms. It may also be programmed to increase signal-to-noise ratio (SNR) by rejecting out-of-band noise frequencies. It may also be programmed to operate as a matched filter to maximize the output SNR relative to a selected transmit waveform shape. The invention is capable of operating with time-interleaved data samples associated with multiple beams.

In another aspect of the method and apparatus of the invention, the baseband processor may operate as a sample rate converter which converts the sample rate of the receive beamformer signal to a rate that is advantageous for an image display processor.

In another aspect of the method and apparatus of the invention, the baseband processor includes a programmable complex multiplier which follows the programmable filter. The complex multiplier corrects systematic processing amplitude and phase differences between scan lines so that there is scan-line-to-scan-line (beam-to-beam) amplitude coherence (also called amplitude matching) and phase coherence (also called phase alignment). Such an aspect supports the novel feature of synthesizing samples and synthetic scan lines as described and claimed in the referenced co-pending patent application entitled: METHOD AND APPARATUS FOR COHERENT IMAGE FORMATION.

The method and apparatus further supports adjustable frequency scanning in order to mitigate grating lobes as presented in co-pending patent application entitled: METHOD AND APPARATUS FOR ADJUSTABLE FREQUENCY SCANNING IN ULTRASOUND IMAGING. The complex multiplier in another aspect can provide frequency remodulation of scan line data to maintain scan-line-to-scan-line phase coherence as the frequency changes while scanning.

In still another aspect of this invention, the baseband processor can track receive signal frequency downshifting with tissue depth due to attenuation.

Additional advantages, objects, and novel features can be obtained from a review of the specification and the figures.

BRIEF DESCRIPTION OF THE FIGURES

FIGS. 2b and 2c taken together depict a block diagram of the ultrasound beamformer system of FIG. 2a.

FIG. 7 illustrates the waveform response at the same range point for three ultrasound scan lines.

FIG. 8 illustrates the method of phase accumulation at range $r_t$ for a Vector scan geometry in which the phase differences for actual acquired scan lines (solid) at nominal line spacing are indicated. The dashed lines indicate target scan lines which were not acquired.

DETAILED DESCRIPTION OF THE PRESENTLY PREFERRED EMBODIMENTS

The present invention comprises a component of a medical ultrasound imaging system for which additional patent applications, listed above, have been simultaneously filed in the United States Patent and Trademark Office.

A. Overview of Preferred Beamformer System Architecture

1. Ultrasound Signal Description

Figure 1A:
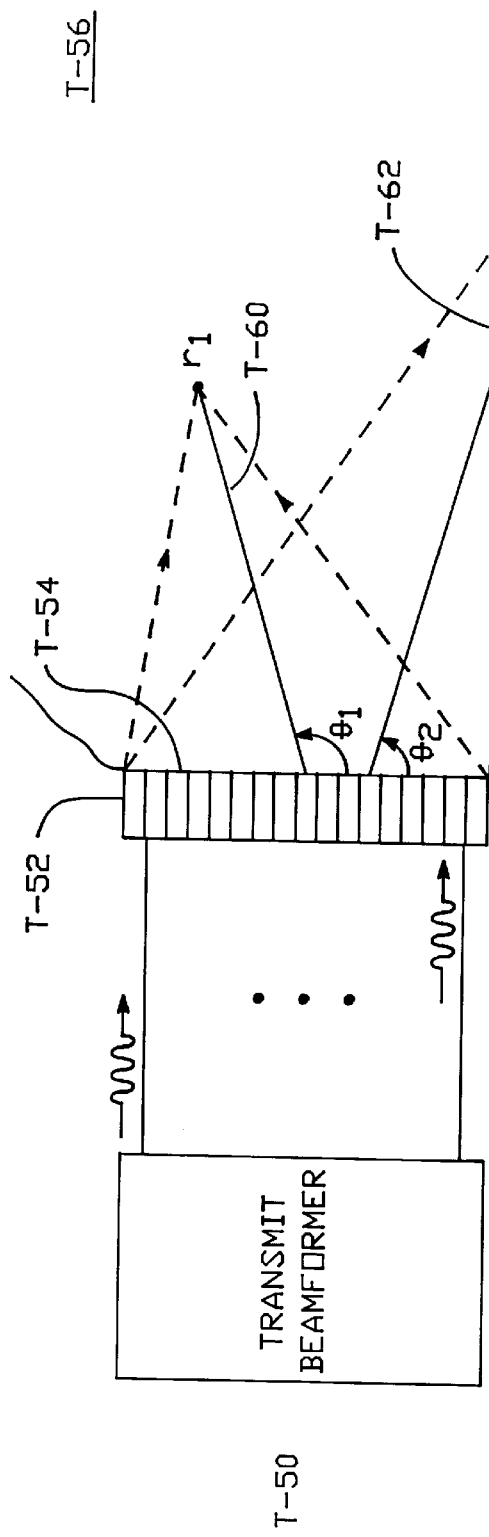
FIGS. 1a and 1b conceptually depict the transmission and reception of ultrasound beams to and from body tissue.
Figure 1B:
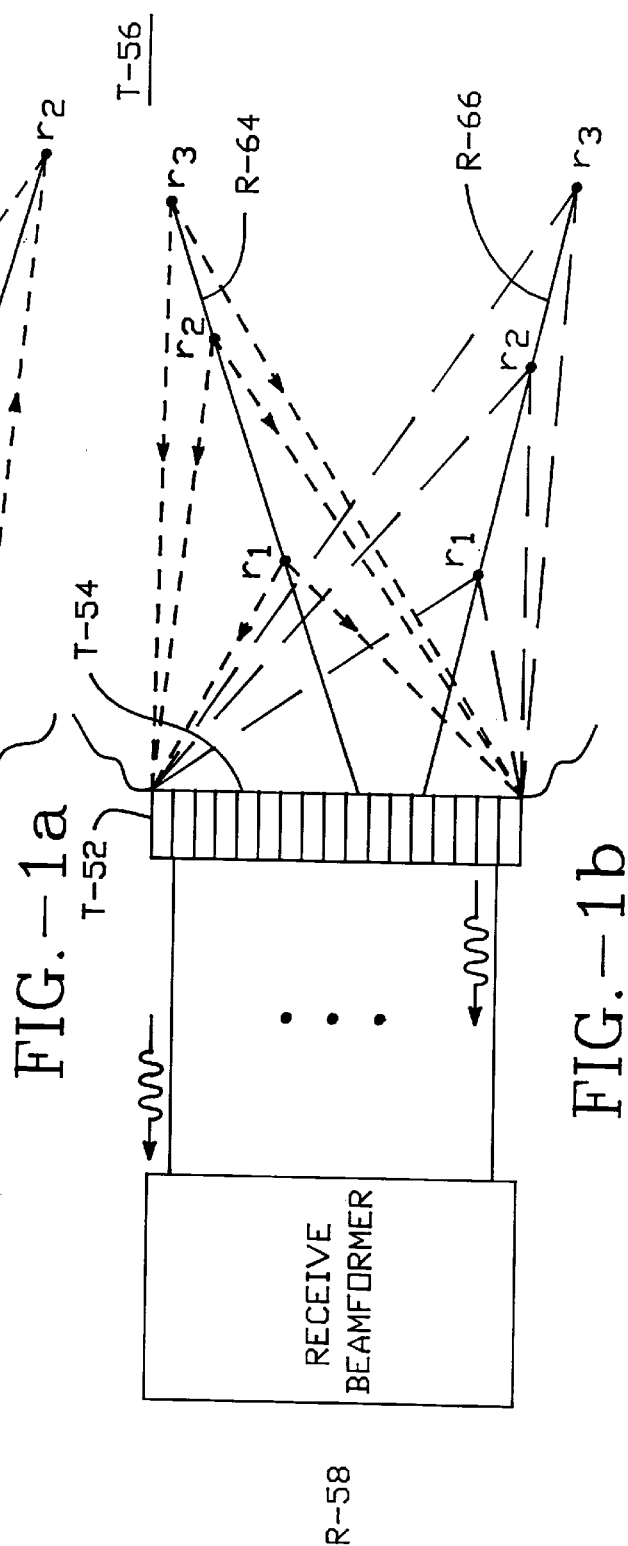

Referring now to the drawings, FIGS. 1a and 1b depict representations of transmit and receive scan lines (solid) and straight-line signal propagation paths from individual elements (dashed), respectively. In FIG. 1a, the transmit beamformer is generally identified by T-50 with the transducer array T-52 containing a multiplicity of individual transducer elements T-54 organized as a linear phased array in this particular embodiment. As is known in the art, there are a great variety of transducer array configurations available for use with ultrasound transmit and receive beamformer systems. As can be seen in FIG. 1a, the transmit beamformer T-50 sends appropriately time-delayed electrical signals to the individual transducer elements T-54. These transducer elements T-54 then in turn convert electrical signals into acoustic waves that propagate into the body tissue T-56. By applying different time delays to the excitation signals sent to the individual transducer elements T-54, transmit scan lines T-60 and T-62, having respective foci $r_1$ and $r_2$, can be established. It is to be understood that each of these transmit scan lines is representative of a center line of a different transmit beam which is steered and focused into the body to be imaged.

The transmit beamformer T-50 can generate simultaneous multiple beams along different scan lines, or different focal depths along the same scan line (compound focus). Further, the multiple transmit beams can each scan the entire image format or be transmitted such that each of the multiple beams only scans a specified section of the image format.

FIG. 1b depicts a digital receive beamformer R-58 which is also connected to the transducer array T-52. Also depicted in FIG. 1b are receive scan lines R-64, R-66 corresponding to a dynamically focused first receive beam and a dynamically focused second receive beam, respectively. The beams are sampled in range at a plurality of focal depths ($r_1, r_2, r_3$) along each scan line. In the digital receive signal path of the present invention, transducer array signals can be selectively separated into data representative of multiple individual beams.

Each scan line of a transmit or receive scan pattern can be parameterized by the origin on the transducer array, the scan line orientation (angle θ) and the focus depth or range (r). The ultrasound imaging system of the present invention stores a pre-computed sparse data set of focusing time delay and aperture apodization values indexed by these parameters (based on geometric considerations as is known in the art) and expands the values by real-time computational means to control the transmit and receive beamformation systems that produce the desired scan lines.

2. Beamformer System

Figure 2A:
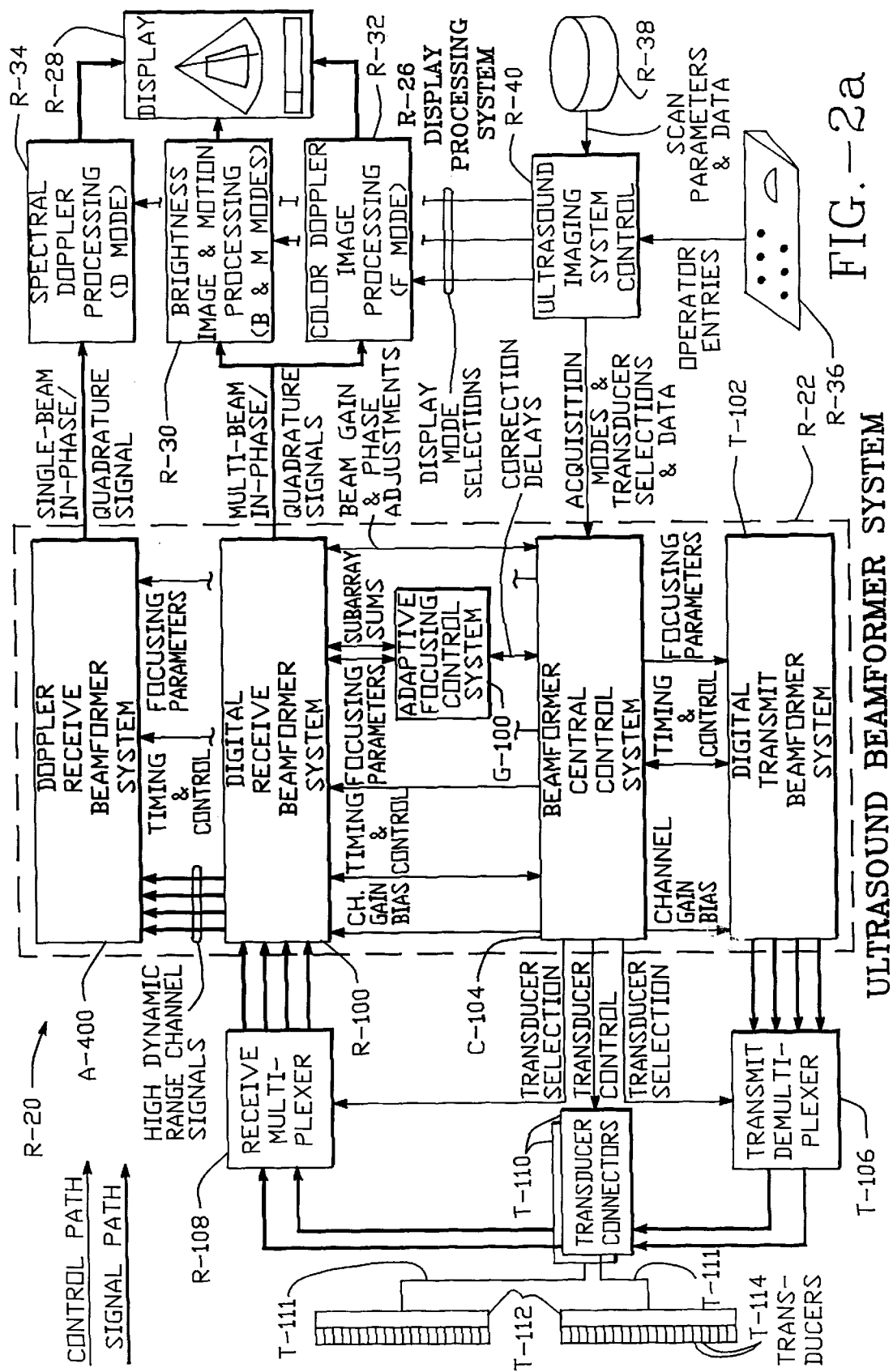
FIG. 2a depicts a block diagram schematic of a novel ultrasound beamformer system of an ultrasound medical imaging system including an embodiment of a baseband processor system of the invention.
Figure 2B:
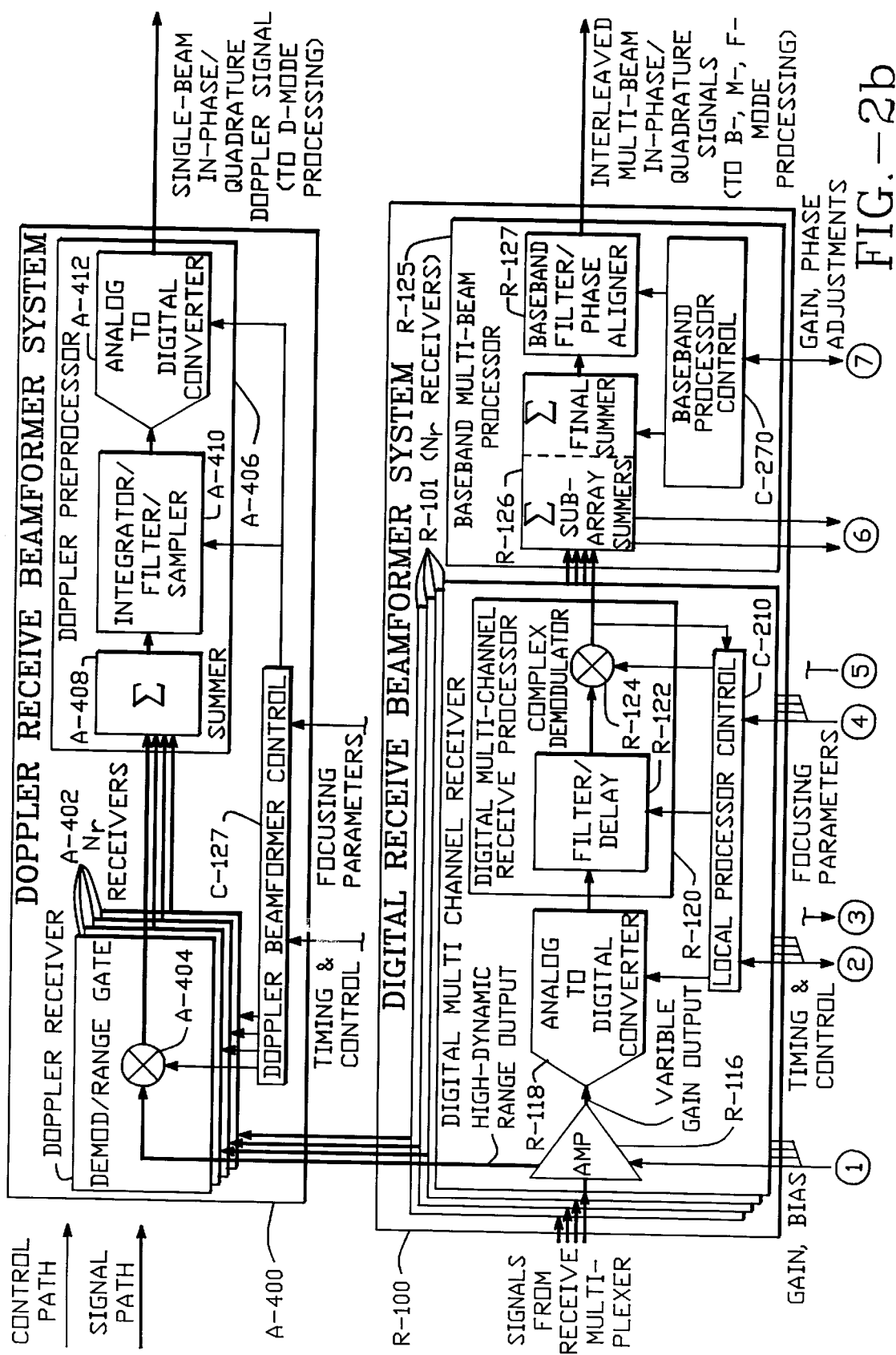
Figure 2C:
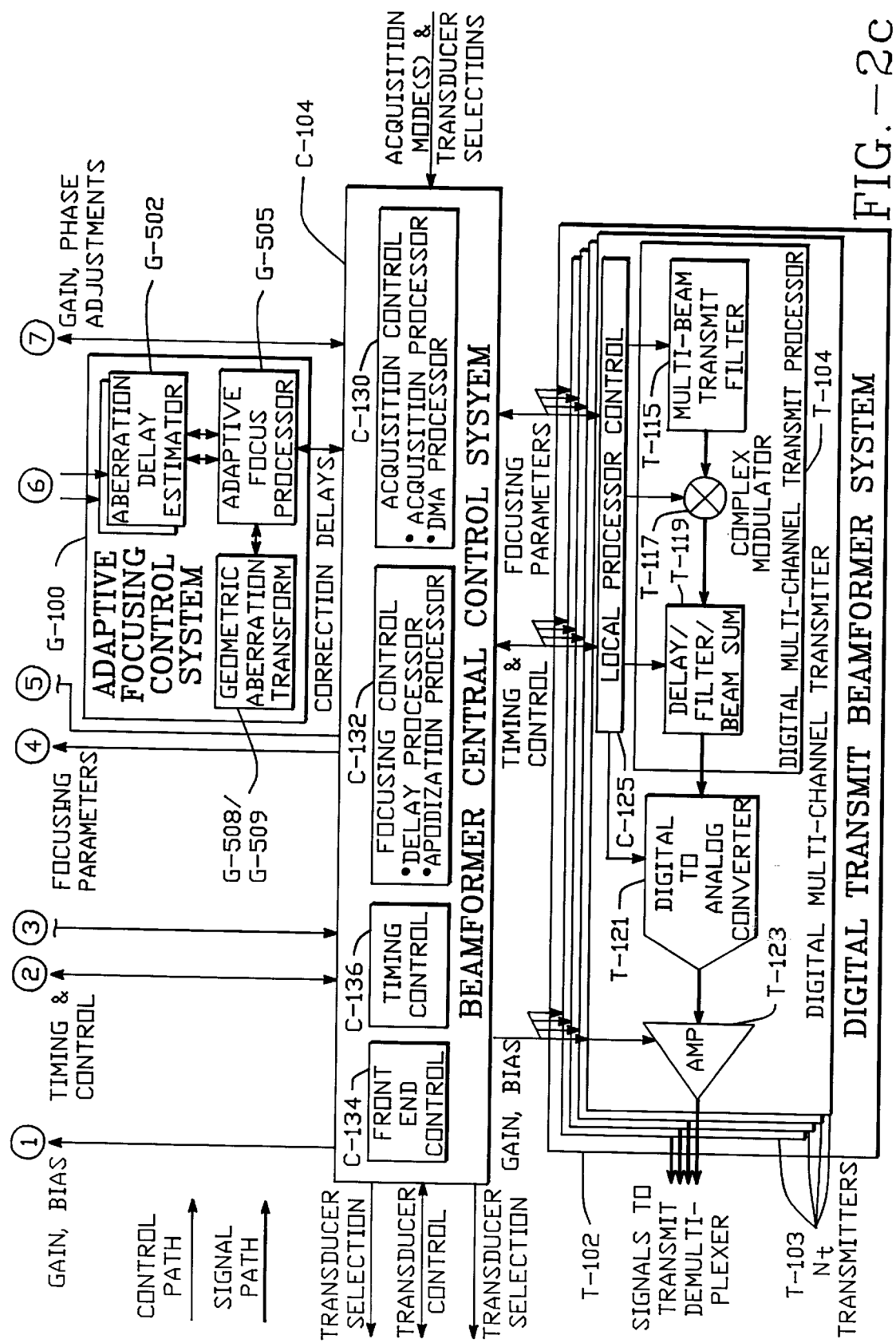

FIGS. 2a, 2b, 2c depict an overall block diagram of a medical ultrasound imaging system R-20. Ultrasound system R-20 includes a beamformer system R-22, one or more transducers T-112, a display processing system R-26 with a display R-28 and an ultrasound imaging system control R-40. As used herein, the term ultrasonic refers to frequencies above the range of human hearing. However, the transducer arrays T-112 are optimized for frequencies typically within the range of 2–10 MHz.

In FIGS. 2*a*, 2*b*, or 2*c*, the beamformer system R-22 includes inventive and novel (1) digital transmit beamformer system T-102, (2) digital receive beamformer system R-100, (3) beamformer central control system C-104, (4) adaptive focusing control system G-100, (5) Doppler receive beamformer system A-400, (6) baseband multi-beam processor R-125, and (7) coherent sample synthesizer S-100. These systems are depicted as functional block diagrams. The blocks are abstracted from the actual implementation of a preferred embodiment in order to better illustrate the signal processing functions performed.

In FIGS. 2*a*, 2*b*, 2*c*, the control signals are communicated over the light lead lines while the signal paths are depicted with heavy lead lines.

As indicated in FIG. 2*a*, beamformer system R-22 provides two sources of digital beam data to the display processing system R-26: (1) Doppler receive beamformer single-beam complex in-phase/quadrature data representing coherent temporal sampling of the beam (CW case) or coherent temporal sampling at one range location along the beam (PW case), and (2) digital receive beamformer multi-beam complex in-phase/quadrature data representing coherent sampling in range along each receive scan line. Beamformer system R-22 can be operated to provide a sequence of scan lines and associated samples as above to provide data for a variety of display modes. By way of example, possible display modes and their associated processors include (1) brightness image and motion processor R-30 for B-mode (gray-scale imaging) and M-mode (motion display), (2) color Doppler image processor R-32 for flow imaging, and (3) spectral Doppler processor R-34 for wide dynamic nonimaging Doppler velocity vs. time displays. Additional display modes can be created from the two complex data sources of R-22, as will be obvious to those skilled in the art.

Ultrasound system R-20 also includes a transmit demultiplexer T-106 for routing the output waveforms from the transmitters T-103 to the transducer elements T-114, a receive multiplexer R-108 for routing the input waveforms from the transducer elements T-114 to the receivers R-101, one or more transducer connectors T-110 and transducer arrays T-112. Many types of transducer arrays can be used with the present system.

Ultrasound system R-20 also includes an ultrasound imaging system control R-40, archival memory R-38 for storing scan parameters and scan data, and operator interface R-36.

The transducer array T-112 is interchangeable with a variety of different kinds of transducer arrays, including but not limited to linear, curved, curvi-linear and annular transducer arrays. A variety of transducer array shapes and frequencies are desirable in order to satisfy the requirements of a variety of different clinical settings. However, the transducer arrays T-112 are typically optimized for frequencies within the range of 2–10 MHz. The medical ultrasound system R-20 performs the three major functions of driving the ultrasonic transducer array of elements T-114 to transmit focused ultrasound energy, receiving and focusing backscattered ultrasound energy impinging on the transducer array T-114, and controlling the transmit and receive functions to scan a field of view in scan formats including (but not limited to) linear, sector or Vector® format.

3. Digital Transmit Beamformer System

The digital transmit beamformer T-102 (FIG. 2*c*) is the subject of the above-identified application entitled: METHOD AND APPARATUS FOR TRANSMIT BEAMFORMER SYSTEM (Attorney Docket No. 5050-77). In a preferred embodiment, the digital transmit beamformer T-102 is comprised of a plurality of digital multi-channel transmitters T-103, one digital multi-channel transmitters for one or more of the individual transducer elements T-114. The transmitters are multi-channel in that each transmitter can process, in a preferred embodiment, up to four independent beams. Thus, for example, 128 multi-channel transmitters have 512 channels. In other preferred embodiments, more than four independent beams can be achieved. Processing more than four beams per processor is within the scope of the invention.

In a preferred embodiment, each of the digital multi-channel transmitters T-103 produces as its output in response to an excitation event the superposition of up to four pulses, each pulse corresponding to a beam. Each pulse has a precisely programmed waveform, whose amplitude is apodized appropriately relative to the other transmitters and/or channels, and delayed by a precisely defined time delay relative to a common start-of-transmit (SOT) signal. Transmitters T-103 are also capable of producing CW.

Each digital multi-channel transmitter T-103 conceptually comprises a multiple beam transmit filter T-115 which provides an output to a complex modulator T-117. The output from complex modulator T-117 is communicated to a delay/filter block T-119, and therefrom is provided to a digital-to-analog converter (DAC) T-121. The output of the DAC T-121 is amplified by an amplifier T-123. The multiple beam transmit filter T-115, the complex modulator T-117 and the delay/filter block T-119 comprise a digital multi-channel transmit processor T-104.

The transmit filter T-115 can be programmed to provide any arbitrary real or complex waveform responsive to a start-of-transmit (SOT) signal. The transmit filter T-115 is implemented with a memory which stores real or complex samples of any desired and arbitrary pulse waveform, and a means of reading the samples out sequentially in response to the start-of-transmit (SOT) signal delayed by a component of the focusing delay. In a preferred embodiment, the memory of T-115 is programmed to store baseband representations of real or complex pulse envelopes.

Block T-115, although primarily a memory, is referred to herein as a transmit filter, as the output of block T-115 can be thought of as the time response of a filter to an impulse. The complex modulator T-117 upconverts the envelope to the transmit frequency and provides appropriate focusing phase and aperture apodization.

Delay/filter block T-119 conceptually provides any remaining focusing delay component and a final shaping filter. The digital-to-analog converter (DAC) T-121 converts the transmit waveform samples to an analog signal. The transmit amplifier T-123 sets the transmit power level and generates the high-voltage signal which is routed by the transmit demultiplexer T-106 to a selected transducer element T-114.

Associated with each multi-channel transmit processor T-104 is a local or secondary processor control C-125 which provides control values and parameters, such as apodization and delay values, to the functional blocks of multi-channel transmit processor T-104. Each local or secondary channel control C-125 is in turn controlled by the central or primary control system C-104.

4. Digital Receive Beamformer System

The digital receive beamformer R-100 (FIG. 2b) is the subject of the above-identified application entitled: METHOD AND APPARATUS FOR RECEIVE BEAMFORMER SYSTEM (Attorney Docket No. 5050-77).

The signals from the individual transducer elements T-114 represent return echoes or return signals which are reflected from the object being imaged. These signals are communicated through the transducer connectors T-110 to the receive multiplexer R-108. Through multiplexer R-108, each transducer element T-114 is connected separately to one of the plurality of digital multi-channel receivers R-101 which taken together with summer R-126 comprise the digital receive beamformer R-100 of the invention. The receivers are multi-channel in that each receiver can process, in a preferred embodiment, up to four independent beams. Processing more than four beams per processor is within the scope of the invention.

Each digital multi-channel receiver R-101 can, in a preferred embodiment, comprise the following elements which are represented by the function block diagram in FIG. 2b. These elements include a dynamic low-noise and variable time-gain amplifier R-116, an analog-to-digital converter (ADC) R-118, and a digital multi-channel receive processor R-120. The digital multi-channel receive processor R-120 conceptually includes a filter/delay unit R-122 and a complex demodulator R-124. The filter/delay unit R-122 provides for filtering and coarse focusing time delay. The complex demodulator R-124 provides for fine focusing delay in the form of a phase rotation and apodization (scaling or weighting), as well as signal demodulation to or near baseband. The digital multi-channel receivers R-101 communicate with summer R-126 where the signal samples associated with each beam from each receive processor are summed to form final receive scan line samples, and the resulting complex samples provided to baseband processor R-125. The exact functioning and composition of each of these blocks will be more fully described below.

A local or secondary control C-210 is associated with each digital multi-channel receiver R-101. Local processor control C-210 is controlled by central or primary control C-104 and provides timing, control and parameter values to each said receiver R-101. The parameter values include focusing time delay profiles and apodization profiles.

5. Doppler Receive Beamformer System

The Doppler receive beamformer system A-400 for wide dynamic range, nonimaging Doppler acquisition includes analog receivers A-402, each of which receives echo signals from a respective one or more transducers T-114. Each of the Doppler receivers A-402 includes a demodulator/range gate A-404 which demodulates the received signal and gates it (PW mode only) to select the echo from a narrow range. The analog outputs of the Doppler receivers A-402 are communicated to a Doppler preprocessor A-406. In preprocessor A-406, the analog signals are summed by summer A-408 and then integrated, filtered, and sampled by analog processor A-410. Preprocessor A-406 then digitizes the sampled analog signal in an analog-to-digital converter (ADC) A-412. The digitized signal is communicated to the display processing system R-26. The Doppler receive beamformer system is the subject of a co-pending patent application entitled: METHOD AND APPARATUS FOR DOPPLER RECEIVE BEAMFORMER SYSTEM.

Associated with all Doppler receivers A-402 is a single local or secondary Doppler beamformer control C-127. Doppler beamformer control C-127 is controlled by central or primary control system C-104 and provides control and focusing parameter values to the Doppler receive beamformer system A-400.

The present beamformer system R-22 advantageously combines an imaging digital receive beamformation system R-100 and the nonimaging Doppler receive beamformation system A-400 in a manner which uses the same digital transmit beamformation system T-102 and the same transducer array. This arrangement allows the digital receive beamformation system R-100 to be optimized for imaging modes such as B-mode and color Doppler imaging, and therefore has high spatial resolution, while the accompanying Doppler receive beamformation system has a wide dynamic range and may be optimized for use in acquiring signals for nonimaging Doppler processing.

6. Beamformer Central Control System

The beamformer central control system C-104 of the present invention controls the operation of the digital transmit beamformer system T-102, the digital receive beamformer system R-100, the Doppler receive beamformer system A-400, the adaptive focusing control system G-100, and the baseband processor R-125. The beamformer control is more fully discussed in the above referenced and incorporated patent application entitled: METHOD AND APPARATUS FOR FOCUS CONTROL OF TRANSMIT AND RECEIVE BEAMFORMER SYSTEMS.

The main control functions of the central control system C-104 are depicted in FIG. 2c. The control functions are implemented with four components. The acquisition control C-130 communicates with the rest of the system including the ultrasound system control R-40 and provides high level control and downloading of scanning parameters. The focusing control C-132 computes in real time the dynamic delay and apodization digital values required for transmit and receive beamformation, which includes pre-computed and expanded ideal values plus any estimated correction values provided by adaptive focusing control system G-100. The front end control C-134 sets the switches for the demultiplexer T-106 and the multiplexer R-108, interfaces with the transducer connectors T-110, and sets the gain and bias levels of all transmitter amplifiers T-123 and all receive amplifiers R-116. The timing control C-136 provides all the digital clocks required by the digital circuits. This includes the sampling clocks for all the transmitter DACs T-121 and receiver ADCs R-118.

In a preferred embodiment central control C-104 expands sparse tables of focusing time delay and aperture apodization values based on pre-computed and stored data, through such techniques as interpolation and extrapolation. The expanded delay and apodization values are communicated to the local processor controls as a profile of values across the transducer aperture where the delay and apodization data expansion in range is completed to per-transducer-element, per-sample, per-beam values.

7. Adaptive Focusing Control System

Adaptive focusing control system G-100 provides for real time concurrent adaptive focusing. Adaptive focusing control system G-100 is comprised of an adaptive focus processor G-505 which provides focus correction delay values to the focus control C-132 of the central control C-104. Adaptive focus processor G-505 operates on output produced by aberration value estimators G-502 from data gathered from the subarray summers R-126 of the digital receive beamformer system R-100. Accordingly, aberration correction values, preferably aberration delay and amplitude values, are adaptively measured for each receive scan line or for a subset of receive scan lines in range regions corresponding to transmit focal depths by the adaptive focusing control subsystem G-100 shown in FIG. 2c. Adaptive focusing control system G-100 is more fully described in co-pending patent application entitled: METHOD AND APPARATUS FOR REAL TIME, CONCURRENT ADAPTIVE FOCUSING IN AN ULTRASOUND BEAMFORMER IMAGING SYSTEM.

It is to be understood that in addition to the adaptive focusing control system which adjusts focus delays, that a number of adaptive control systems are contemplated. These systems, by way of example, include (1) adaptive contrast enhancement control system for adjusting focus delays and aperture apodizations, (2) adaptive interference cancellation control for adjusting focus delays and phases, aperture apodizations, and (3) adaptive target enhancement control for adjusting focus delays and phase, aperture apodizations, imaging transmit and receive frequencies and baseband waveform shaping.

Another aspect of adaptive focusing which can be included in the preferred embodiment of the adaptive focusing control system G-100 is a geometric aberration transform device G-508/509 which can provide aberration correction delay values to the adaptive focus processor G-505 for scan lines and scan line depth locations for which measured aberration values were not collected by aberration value estimators G-502. More specifically, measured aberration correction values are written to a delay table in G-508/509. G-508/509 retrieves values from the delay table according to look-up rules of the geometric aberration transform to form focusing delay correction profiles across the aperture valid for depths, scan geometries, and acquisition modes other than the depth, scan geometry, and mode for which aberration correction values were measured. The geometric aberration transform device G-508/509 is the subject of co-pending U.S. patent application entitled: METHOD AND APPARATUS FOR A GEOMETRIC ABERRATION TRANSFORM IN AN ADAPTIVE FOCUSING ULTRASOUND BEAMFORMER SYSTEM.

8. Baseband Processor System

The baseband processor R-125 provides for filtering, and receive-scan-line-to-receive-scan-line (beam-to-beam) amplitude and phase adjustments as discussed herein and in the above-referenced patent applications entitled: METHOD AND APPARATUS FOR COHERENT IMAGE FORMATION, and METHOD AND APPARATUS FOR ADJUSTABLE FREQUENCY SCANNING IN ULTRASOUND IMAGING.

The baseband processor R-125 additionally includes a baseband filter, a complex multiplier, and a baseband processor control which controls the operation of the baseband filter and complex multiplier. The baseband processor control is controlled by central control C-104.

9. Coherent Sample Synthesizer System

The coherent sample synthesizer system S-100 (FIG. 2a) is the subject of the above-identified application entitled: METHOD AND APPARATUS FOR COHERENT IMAGE FORMATION.

This system exploits the multi-beam transmit and multi-beam receive capability of the invention to acquire and store coherent (pre-detection) samples of receive beam data along actual scan lines and to perform interpolation of the stored coherent samples to synthesize new coherent samples at new range locations along existing scan lines or along synthetically-created scan lines. Both acquired and synthesized samples are passed to the display processing system R-26.

10. Transmit and Receive Multiplexers

The connectivity between the transducer array elements T-114 and the processors T-103, R-101, A-402 of the digital transmit, digital receive, and Doppler receive beamformer systems is established through a transmit demultiplexer T-106 and a separate receive multiplexer R-108, as shown in FIG. 2a. The multiple-transducer multiplexer configuration shown in FIG. 2a permits selection of transmit and receive apertures lying entirely within a single transducer array or straddling across two transducer arrays. The two multiplexers are independently controlled by the beamformer central control system C-104 and may be programmed to support a number of acquisition modes, including sliding aperture and synthetic aperture modes. The multiplexers and their connectivity are the subject of the above-cited co-pending application entitled: METHOD AND APPARATUS FOR BEAMFORMER SYSTEM WITH VARIABLE APERTURE.

B. Baseband Processor System Preferred Embodiments

The digital baseband multi-beam processor R-125 (FIG. 3) comprises a baseband filter R-127, a complex multiplier B-254, and a baseband processor control C-270.

1. Baseband Filter and Complex Multiplier

The complex baseband beam signal (or time-interleaved beam signals in the multiple beam case) from the digital receive beamformer system R-100 is communicated to the baseband multi-beam processor R-125. The baseband filter R-127 performs filtering, signal shaping, and/or sample rate conversion by a factor L/M, where L is the integer interpolation factor and M is the integer decimation factor. Complex multiplier B-254 provides for (1) scan-line-dependent and range-dependent amplitude and phase adjustments of the filtered I/Q signal B-260 required to correct for amplitude and phase differences resulting from scan-line-to-scan-line apodization changes, scan geometry, and non-aligned effective transmit and receive origins, and (2) remodulation (frequency adjustment) of the filtered signal to correct for phase variations in range resulting from different transmit frequencies per scan line. The advantage of the use of a scan-line-to-scan-line variable frequency mode on transmit and receive beamformation is the reduction of grating lobes (see co-pending application entitled: METHOD AND APPARATUS FOR ADJUSTABLE FREQUENCY SCANNING IN ULTRASOUND IMAGING, which discusses a scan-line-to-scan-line variable frequency mode).

Such amplitude, phase, and frequency adjustments between scan lines, particularly two or more adjacent scan lines, is, for example, for purposes of creating coherent samples needed to implement coherent image processing techniques as described in the above co-pending application entitled: METHOD AND APPARATUS FOR COHERENT IMAGE FORMATION. Other post-beamformation operations requiring phase-coherent samples between scan lines will also benefit from the adjustments provided by the complex multiplier.

Baseband filter R-127 preferably includes an upsampler B-255 (FIG. 3), a downsampler B-257, and a multi-tap FIR filter B-256, designated by the impulse response sequence h4[$n$], which is programmable using either real or complex coefficients. The upsampler, working in conjunction with the filter, acts as an interpolator which increases the sample rate by an upsampling integer factor L. The downsampler, working in conjunction with the filter, acts as a decimator which decreases the sample rate by a downsampling integer factor M. When both the upsampler and downsampler are operated, the net sample rate conversion factor is L/M. The sample rate conversion is advantageous for adjusting sample rates to downstream processors, such as the display processing system R-26. In the preferred embodiment, a 16-tap complex coefficient FIR filter will satisfy the various filtering operations for which the baseband filter may be programmed. During sample rate conversion operation, fractionally-shifted versions of the desired filter response in the coefficient registers of the filter are appropriately sequenced during filter operation.

Baseband filter R-127 can additionally accomplish three other tasks. First, baseband filter R-127 can be programmed to increase the signal-to-noise ratio by rejecting out-of-band noise frequencies.

Second, the baseband filter may alternatively be programmed to maximize the signal-to-noise ratio by programming as a matched filter or quasi-matched filter design, preferably for matching to substantially Gaussian-shaped transmit pulses as well as pulses of other shapes. Gaussian-shaped pulses are especially useful as they represent waveforms that do not distort during transmission through attenuative media such as the body.

Third, baseband filter R-127 enables pulse equalization and shaping by compensating for both the transducer frequency response and the analog signal path prior to the ADC R-118.

2. Baseband Processor Control

Figure 3:
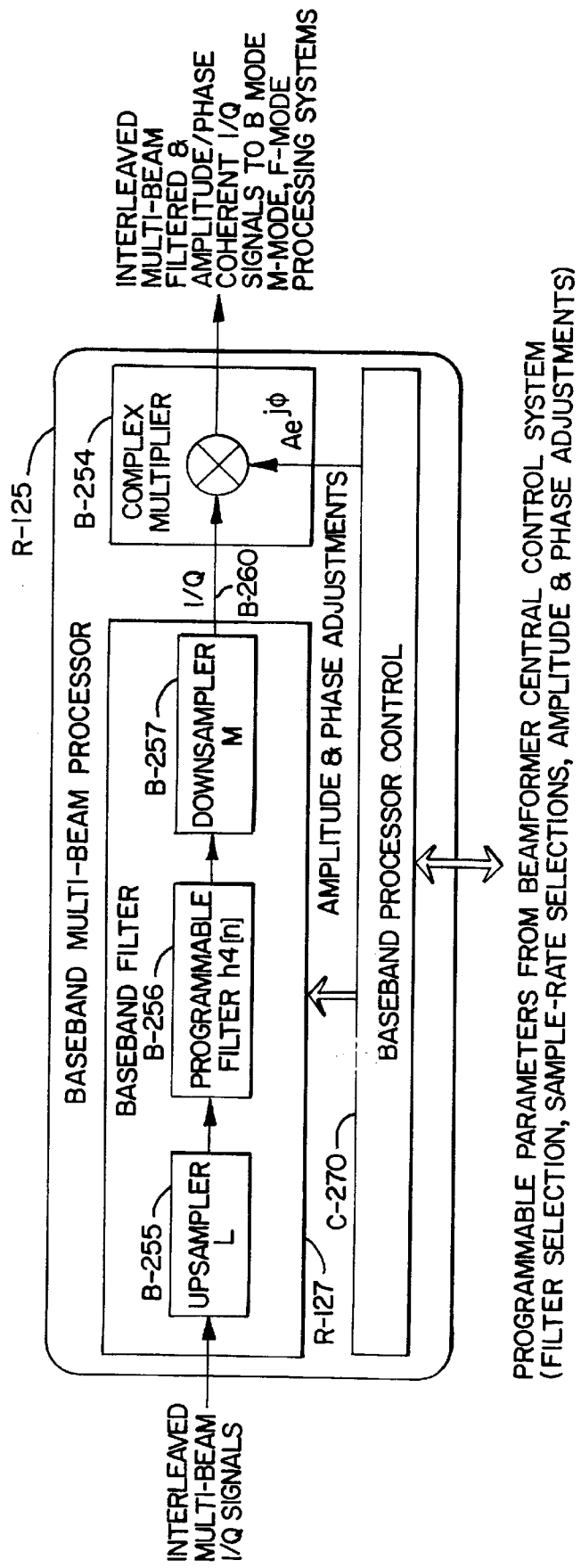
FIG. 3 depicts a block diagram of an embodiment of a digital baseband multi-beam processor for the receive beamformer of FIG. 2.

The filter coefficients h4[n], decimation factor M, and interpolation factor L for baseband filter R-127 are programmed into baseband processor R-125 by being downloaded from the central control C-104 to coefficient and rate memory C-278 (FIG. 5) in the baseband processor control C-270 (FIG. 3). The downloaded filter coefficients and sample rate conversion factors can be changed at any time by introducing new coefficients and factors into the central control C-104. The coefficients and factors stored in the coefficient and rate memory C-278 are selectable by the central control C-104 for programming the filter and sample rate conversion ratio L/M of the baseband filter R-127.

Following complex multiplier B-254 is a register C-296 which stores scan line sample data so that it can be reported to the DMA processor C-202 of the central control C-104 for providing scan-line-to-scan-line calibration. This calibration function is discussed in the co-pending application: METHOD AND APPARATUS FOR RECEIVE BEAMFORMER SYSTEM (Attorney Docket No. 5050-77).

Figure 5:
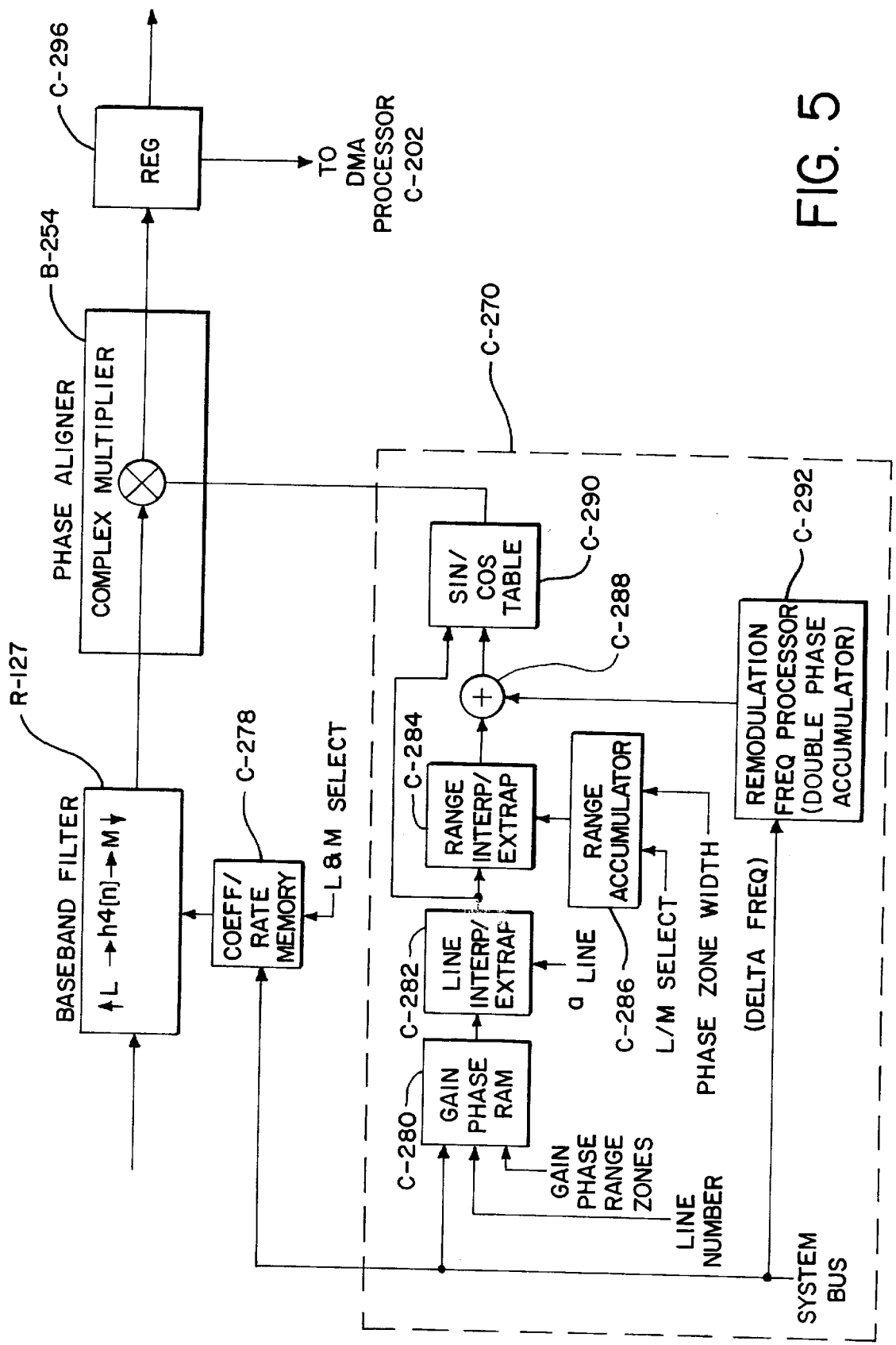
FIG. 5 is a block diagram of an embodiment of the baseband processor control of the invention which provides for filtering and amplitude/phase adjustment among receive scan lines.

The complex multiplier B-254 includes a control function which is contained in baseband processor control C-270 (FIG. 5). In baseband processor control C-270, a scan-line-to-scan-line (beam-to-beam) amplitude adjustment value A and a phase adjustment value φ per sample of each beam is generated in a time-interleaved manner corresponding to the time-interleaved beam samples B-260. As discussed above, the phase correction value φ is the sum of phase terms that include: (1) a phase adjustment term required to correct for phase differences due to scan-line-to-scan-line apodization changes, (2) a phase adjustment term for scan geometry which results in non-aligned effective transmit and receive origins (the scan-line-dependent and range-dependent phase adjustment term), and (3) a phase term required to remodulate the signal as though each scan line had been transmitted and received at a common carrier frequency. As discussed herein and in co-pending U.S. patent applications entitled: METHOD AND APPARATUS FOR TRANSMIT BEAMFORMER SYSTEM and METHOD AND APPARATUS FOR ADJUSTABLE FREQUENCY SCANNING IN ULTRASOUND IMAGING, using a frequency scaling factor or frequency vernier factor, each beam can be produced with a different carrier frequency. The complex multiplier accordingly provides for remodulation of the received beam signals between scan lines so that all beams are adjusted to account for any differences in carrier frequencies.

Figure 6A:
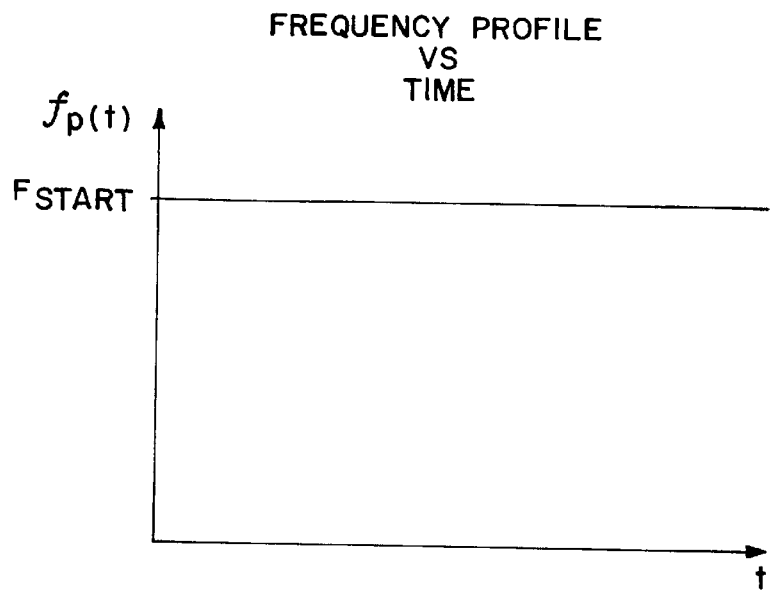
FIGS. 6a, 6b and 6c depict graphs of typical signal frequency downshifting profiles that can be applied for signal remodulation in the baseband processor.
Figure 6B:
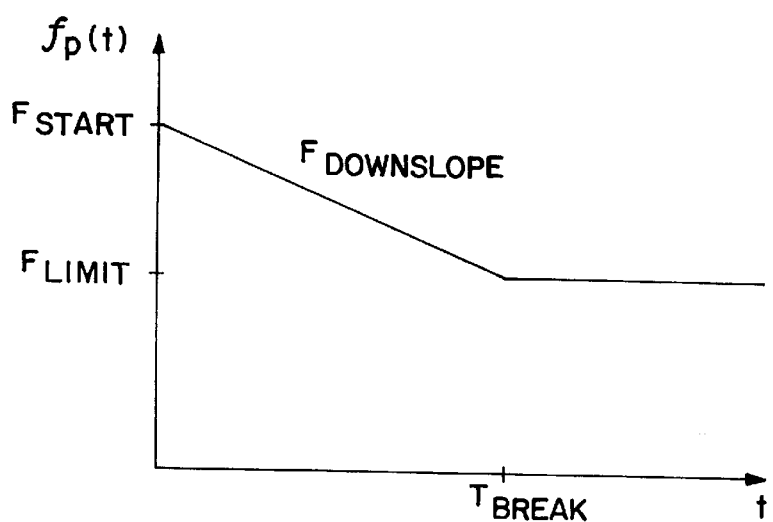
Figure 6C:
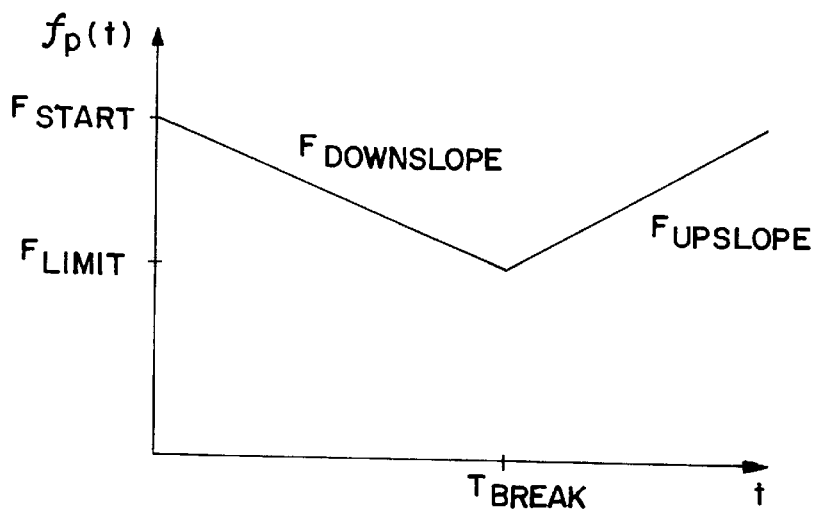

In operation a source data set including scan format geometry parameters, sparse scan line gain and delay values, interpolation coefficients for expanding the sparse values, interpolation factor L, and decimation factor M are downloaded from the central control C-104 to the baseband processor control C-270. Additionally, frequency parameters used in the frequency profile generator of the central control C-104 in accordance with FIGS. 6a, 6b and 6c are downloaded to the baseband processor control C-270. These profiles account for frequency attenuation with depth.

The baseband processor control C-270 of FIG. 5 includes a gain and phase RAM C-280, a scan-line-indexed interpolator C-282 which is supplied with pre-calculated and pre-stored line interpolation coefficients ($\alpha_{line}$) by the central control C-104, and a range-indexed interpolator C-284 with a range accumulator C-286, which is supplied with a rational sample rate conversion factor L/M and a phase zone width, both of which values are pre-calculated and pre-stored in the central control C-104. The rational sample rate conversion factor L/M is the same L and M values supplied to the baseband filter R-127. Additionally as is known in the art, a sample rate conversion in accordance with the rational sample rate conversion factor L/M is accomplished in order to match the input sample data rate to the baseband filter R-127 with the output sample data rate to the display processing system R-26.

Alternatively the range-indexed interpolator/extrapolator C-284 can be supplied with programmable interpolation/extrapolation coefficients which are, by way of example, either (1) pre-calculated and pre-stored in or calculated by the central control or (2) calculated locally in baseband processor control C-270 by a coefficient generator.

The baseband processor control C-270 also includes a remodulation frequency processor C-292 which is preferably implemented as a double phase accumulator. The double phase accumulator calculates phase adjustment values to correct for scan-line-to-scan-line frequency differences and thus remodulates the signal as though a common carrier frequency had been used across all scan lines.

To understand the basis of the remodulation operation, consider an idealized representation of a signal at the output of a beamformer which has been coherently summed across multiple elements, and has undergone modulation on transmit, demodulation on receive, and coherent summation:

$$x(t-2r/c)=e(t-2r/c)\cdot e^{j[\omega_m(t-2r/c)]}\cdot e^{-j[\omega_d \cdot t]} \qquad (1)$$

where, e(t)=a baseband I/Q signal envelope, $\omega_m=2\pi f_m$=a modulation frequency [MHz], $\omega_d=2\pi f_d$=a demodulation frequency [MHz], r=some imaging depth (range) [cm].

Note that the actual center frequency of the imaging pulse, x(t−2r/c), depends additionally on other things, such as tissue attenuation, filtering in the transmit and receive processing chains, and other effects not explicitly considered in the above equation (1). Also not explicitly included in above equation (1) are the detailed representations of focusing delay and phase adjustments necessary for beamformation, though these could be surmised by those skilled in the art. This detail is not required to motivate the particular results presented here.

The transmit modulation frequency, the receive demodulation frequency, or both, may in general be range dependent. In particular, $\omega_m = \omega_m(R_t)$, and $\omega_d = \omega_d(R_r)$, where $R_t$=the distance from the active array center to the transmit focus, $R_r$=the distance from the active array center to the receive focus.

For a system with dynamic focus, this means that $\omega_d$ is continuously updated.

We now consider a scan line 1 corresponding to a modulation frequency $\omega_m^1$, a demodulation frequency $\omega_d^1$, and a post-beamformer remodulation frequency $\omega_r^1$; and an adjacent scan line 2, with respective modulation, demodulation, and remodulation frequencies $\omega_m^2$, $\omega_d^2$, $\omega_r^2$. It can be shown that the post-beamformed phase difference between these two scan lines as a result of the different modulation, demodulation, and remodulation frequencies can be bounded by an amount $\Delta v$, where $$\Delta v < (\omega_m^2 - \omega_m^1) \cdot T_p - [(\omega_d^2 + \omega_r^2) - (\omega_d^1 + \omega_r^1)] \cdot 2R_r/c \qquad (2)$$

where, $T_p$=the imaging pulse duration at any depth of the receive beamformer signal output.

This expression is valid at the receive focal depth, $R_r$, at the point of post-beamformer remodulation. It is again noted that there may be other terms apart from $\Delta v$ which are needed to ensure phase coherence at the beamformer output apart from the above equation (2). Examples of such other terms include, but are not limited to, terms which account for the offset in the beam origin, such as naturally arise in Vector®, linear, and curved linear formats, particularly with end alignment. As expected, $\Delta v = 0$ when $\omega_m^2 = \omega_m^1$, $\omega_d^2 = \omega_d^1$, and $\omega_r^2 = \omega_r^1$.

We now make the observation, from the above equation (2), that providing for remodulation at the post-beamformer, pre-detected output with a frequency $\omega_r$ permits scan-line-to-scan-line phase coherence by its proper selection. In particular, by selecting $\omega_r^1$ and $\omega_r^2$ such that $$\omega_d^1 + \omega_r^1 = \omega_d^2 + \omega_r^2 \qquad (3)$$

then the second term of equation (2) may be substantially ignored. Note that if $\omega_d$ is range dependent, such as would be the case for a range tracking system, then $\omega_r$ must also be range dependent.

The first term of equation (2), given by $(\omega_m^2 - \omega_m^1) \cdot T_p$ may be readily managed by keeping $(\omega_m^2 - \omega_m^1)$ sufficiently small. As an example, consider the requirement that $\Delta v < \pi/4$, and suppose that, as might be typical, the imaging pulse measured at the point of remodulation for a tracking focused system has a duration that is four cycles of the nominal modulation frequency. Then the required limit on scan-line-to-scan-line frequency variation becomes approximately, from equations (2) and (3), $f_m^2 - f_m^1 < f_m^1/32$. If the nominal modulation frequency is 5 Mhz, then the scan-line-to-scan-line modulation frequency difference is constrained to be less than 0.156 MHz, in this example.

Thus, if post-beamformation, pre-detection receive processing requires beam-to-beam phase coherence for all beams in a scan, then the maximum transmit carrier frequency differential between any two beams in the scan should be chosen to meet the above criteria.

The above relationship (3) defining the remodulation frequencies is independent of the modulation frequencies on transmit. Such independence assumes that both the modulation signal and the demodulation signal for all transmit and receive channels are phase-locked to a common timing clock reference. That is, the phases of all such modulation and demodulation signals are defined relative to a common time reference.

The above relationship (3) also assumes that the modulation frequencies on successive transmit scan lines and the demodulation frequencies on successive receive scan lines are each slowly varying to avoid $2\pi$ phase ambiguities. That is, $f_d^1 \approx f_d^2$ and $f_m^1 \approx f_m^2$. This constraint is consistent with the problem being solved.

The above relationship (3) also assumes a "well-focused" system, wherein any observation made concerning a point in the field of view occurs at a time when the receive focus is at that point (i.e. tracking, or dynamic focus), regardless of whether a target is also at that point.

From the central control C-104, pre-calculated and pre-stored values representing the frequency differences between scan lines (delta frequency values) are sent to the remodulation frequency processor C-292. These frequency difference values are based on frequencies and frequency slopes such as specified in FIGS. 6a, 6b and 6c. By way of example only, let it be assumed that the frequency profiles for two scan lines look like FIG. 6b but with different start frequency, $F_{start}$, values and different downshift slope, $\Delta F_{downslope}$, values. Accordingly, downloaded to baseband processor control C-270 from the central control for the two scan lines are the difference in frequencies between the scan lines and the difference in the rate of change of the frequency profiles over time. These values are calculated by the acquisition processor C-130 based on stored parameters and dependent upon the particular rational conversion factor L/M currently being used. The first accumulator of processor C-292 accumulates the difference in the rates of change of the frequency profiles over time between scan lines while the second accumulator accumulates the difference in the frequencies between the scan lines over time. If there is no difference in the rate of change of the frequency profile over time, (i.e. the profile are the same exact for initially different $F_{start}$ values, or after $T_{break}$ in FIG. 6b when the slope goes to zero) the first accumulator performs no function. With no difference in the rate changes of the frequencies between the scan lines, only the second accumulator accumulates the frequency differences over time resulting in a corrective remodulation phase value per sample.

The phase adjustment due to scan-line-to-scan-line apodization changes, the phase adjustment due to scan geometry which results in non-aligned transmit and receive origins, and the phase adjustment due to remodulating the signal to an effective common carrier frequency are added in a summer C-288 and the summed phase value is then converted in a look-up table C-290 to sine and cosine representations. As part of the look-up table C-290 function, the gain is multiplied by the sine and cosine representations. This complex adjustment value $Ae^{j\phi}$ is provided to complex multiplier B-254 for application to the beam signals B-260.

It is to be understood that other embodiments of the baseband processor control are possible within the scope of this invention.

As indicated above, the complex multiplier B-254 ensures that coherent signal relationships are maintained between scan lines. The transmit samples and the echo or receive samples of the signals from beams are defined as being coherent when sufficient information is stored, preserved, or maintained to enable the samples of the return signals to be phase and amplitude corrected from scan-line-to-scan-line.

The process of actually making the phase and amplitude corrections need not have yet taken place, as long as sufficient information with respect to a reference is maintained When a signal sample is processed coherently, the processing continues to maintain sufficient information to perform phase and amplitude correction at a later time. When two or more samples are processed coherently (e.g., coherently summed), the phase and amplitude corrections necessary to achieve phase and amplitude coherence must have previously been performed.

Coherent processing of two or more signal samples yields significant benefits, such as being able to calculate synthetic samples, as described in the above co-pending application.

Due to beamformer central control C-104 specifying and accounting for all aspects of the transmit and receive signal, the entire beamformer system maintains all signal samples as coherent samples throughout the transmit and receive signal path, until the signal is finally detected in an operation which is external to beamformation.

C. Alternative Embodiments

Figure 4A:
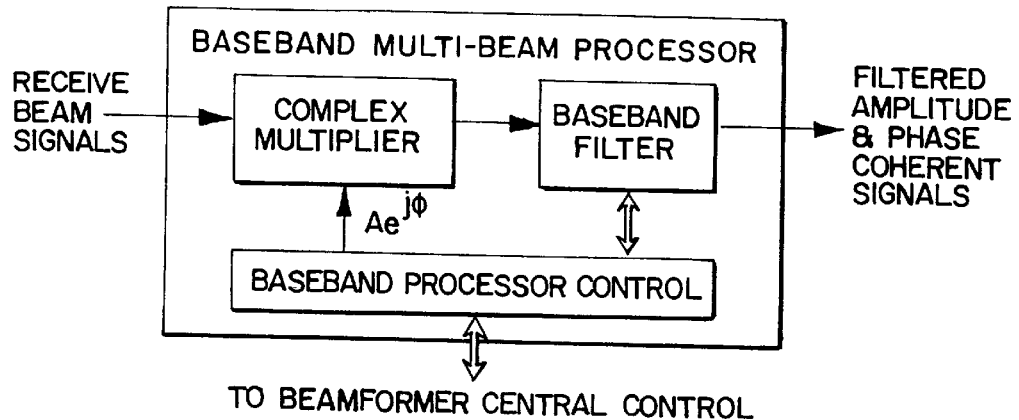
FIGS. 4a and 4b depict alternative embodiments of a baseband processor system. The first alternative in FIG. 4a switches the order of the baseband filter and complex multiplier. The second alternative in FIG. 4b moves the amplitude and phase adjustment into the receive beamformer.
Figure 4B:
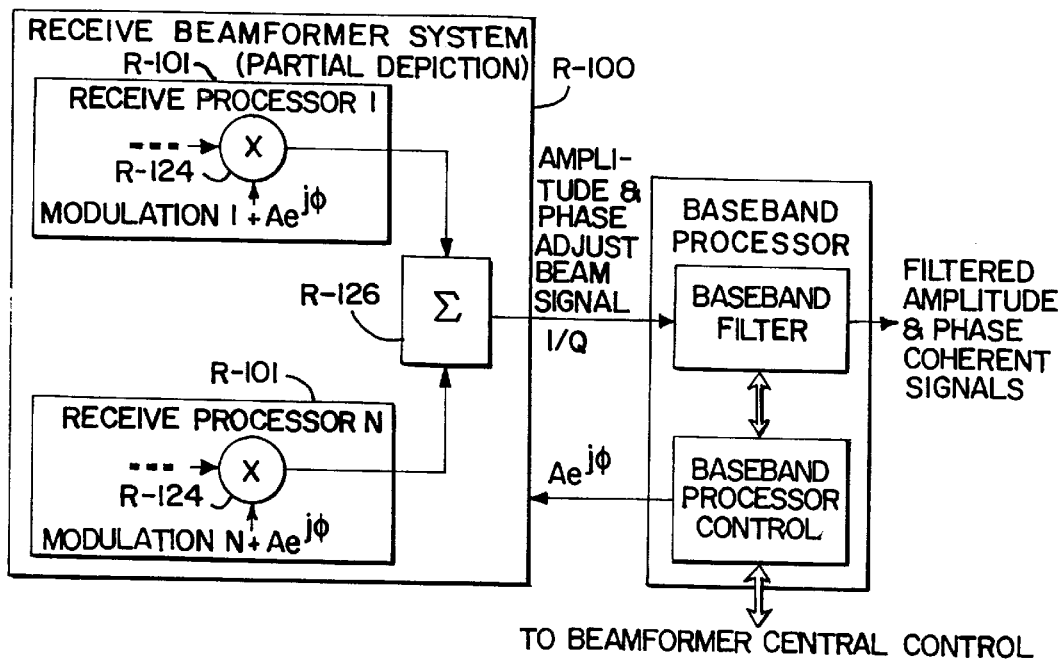

In the preferred embodiment, the amplitude and phase adjustments are accomplished by a complex multiplier following the baseband filter. If $x[n]$ represents a data sample value to be adjusted, then $x[n] \cdot A e^{j\phi}$ is the adjusted value, where A is the amplitude adjustment value and $\phi$ is the phase adjustment value. The same adjustment can be accomplished by moving the complex multiplier in the signal processing path to a position prior to the baseband filter (FIG. 4a). Equivalently, the amplitude and phase adjustment can be provided by moving the operation into each of the receive processors R-101 of the receive beamformer R-100 (FIG. 2b). In particular, the demodulating value applied by each of the complex demodulators R-124 to each receive processor channel sample can be augmented by the amplitude and phase adjustment factor, as illustrated in FIG. 4b. Other embodiments will be obvious to those skilled in the art.

D. Basis for Amplitude and Phase Adjustments

The necessity for amplitude and phase correction, applied after receive beamformation and baseband filtering, can be understood by considering FIG. 7 which shows the scan geometry of two acquired collinear B-mode transmit/receive scan lines with a single target located between these scan lines, at range r along a scan line that passes through the target. The origins and angles of the scan lines are shown, with the dashed line shown on each acquired transmit/ receive scan line pair approximating the wavefront of the transmitted wave at range $r_t$, assuming the apodization used is symmetrical about the scan line origins. The target scan lines, although defined on the same grid as the acoustic acquisition grid, need not coincide with one of the acquired transmit/receive scan lines and, therefore, must be synthetically created by, for example, interpolating between two neighboring acquired transmit/receive scan lines pairs.

The interpolated scan line should appear as if it were an actual scan line responding to the target, using samples at range $r_t$ from the corresponding neighboring scan lines. However, the phase of the return signal at range $r_t$ on each acquired transmit/receive scan line is not the same as the phase that would be measured at range $r_t$ had an actual scan line been acquired coinciding with the target scan line. This is due to the slightly different paths traveled by the waves emanating from each acquired scan line, with origins essentially centered at their apodization centroids, to the target and back. FIG. 7 shows that the two-way path length for scan line 1 is greater than $2r_1$, while the path length for scan line 2 is less than $2r_1$. An additional component contributing to a path length difference arises from the displacement of the apodization centroid from the scan line origin, and leads to additional phase error between the acquired signals along scan line 1 and scan line 2. Therefore, this phase difference between the scan line signals at range $r_t$ from each acquired scan line exists and must be compensated before coherent processing such as interpolation between scan lines is performed. This is illustrated by the return signal waveforms of FIG. 7. Suppose that the phase measured at range $r_t$ along scan line 2 differs by 180° from the phase measured at range $r_t$ along scan line 1, given a target centered between scan line 1 and scan line 2 at range $r_t$. If the amplitudes of the return signals were approximately equal, then interpolation between scan line 1 and scan line 2 at range $r_t$ would yield essentially a zero result. However, if an actual collinear transmit/receive scan line pair were fired along the target scan line, the non-zero response shown by the dashed waveform in FIG. 7 would be the actual result. In general, the phase difference to be compensated by the baseband processor is a function of range and scan line origin and angle.

In general, there are both amplitude and phase differences between acquired scan line signals at a range r, given a target range r along a target scan line, which depend in a complicated relationship on the scan format, array shape, target geometry with respect to the array, transmit/receive apodizations, transmit/receive apodization end-treatment, single firing or multiple firing synthetic scan line formation, frequency, and waveform shape. An approximate closed form expression for the scan line relative response to a reference point amplitude and phase is based on the assumptions that (1) target scan line lies within the main beam of each of the respective scan line pairs, i.e., the transmit and receive scan lines are spaced less than or equal to the Nyquist spacing, and (2) the apodization function is a Gaussian weighting across the array aperture. The relative response at range $r_t$ to an absolute reference phasor ($A e^{j\Phi}$) is another complex phasor that is a function of three major terms. The relative response phasor $\rho(r_t)$ is given by the set of equations in Table 1. Note the list of dependent parameters at the end of Table 1, which include all typical scanning format parameters encountered in ultrasonic imaging.

To compensate for the effect of this difference, complex beam samples could, for example, simply be multiplied by the inverse $1/\rho(r_t)$ before coherent operations on samples at a common range, but different scan lines, is performed. Alternately, only the relative phasor difference between two spatial points in the acquired scan line data needs to be corrected before coherent operations are performed with the data. Assuming a uniform target has been intersected by the scan lines, let $\rho_1 = A_1 \cdot e^{j\psi_1}$ be the relative (to a reference point) complex phasor response at a point 1 along some scan line, and let $\rho_2 = A_2 \cdot e^{j\psi_2}$ be the relative complex phasor response at another point 2 elsewhere (could be the on the same scan line or on another scan line). Ideally, one would like the signal processing performed by the beamformation to yield identical complex beam signal responses everywhere that the uniform target is intersected by the scan lines so that, for example, linear interpolation between any two scan lines samples would yield the identical complex response. When such a condition is achieved, the scan line signal responses are said to be "amplitude coherent" (because $A_1 = A_2$ at the two points) and "phase coherent" (because $\psi_1 = \psi_2$ at the two points). However, geometric conditions of acquisition and the finiteness of apertures produces systematic effects that lead to different complex responses, as Table 1 clearly indicates. One must at least adjust the "relative" response at two points, using for example "complex multiplication" of the point 1 response by $\rho_2/\rho_1$ or "complex multiplication" of the point 2 response by $\rho_1/\rho_2$, before there is amplitude coherence and phase coherence between at least these two spatial locations. Because $\rho_2/\rho_1 = (A_2/A_1)e^{j(\psi_2-\psi_1)}$ or $\rho_1/\rho_2 = (A_1/A_2)e^{j(\psi_1-\psi_2)}$, amplitude coherence is achieved by "amplitude adjustment" using the factor $A_2/A_1$ or $A_1/A_2$, and phase coherence is achieved by "phase adjustment" by the factor $(\psi_2-\psi_1)$ or $(\psi_1-\psi_2)$. The process of achieving phase coherence is also called "phase alignment" because the relative phase between two spatial sample points after phase adjustment is such that $(\psi_2-\psi_1)=0$, that is, the phase responses are "aligned" after adjustment to yield a zero phase difference. The terms complex response adjustment and phase alignment will also be used here to mean that both phase adjustment and amplitude adjustment operations are to be used, unless indicated otherwise.

Because a complex number c may be represented in polar coordinate form as $c = a \cdot e^{j\phi}$ or equivalently as the in-phase and quadrature (I/Q) format $c = x_I + jx_Q$, in which $a = (x_I^2 + x_Q^2)^{1/2}$, $\theta = \arctan(x_I/x_Q)$, $x_I = a \cdot \cos\theta$, $x_Q = a \cdot \sin\theta$, the amplitude and phase adjustments to yield $\rho \cdot c$ using some complex value $\rho$ (or ratio of $\rho$ values) may be performed using a number of means. A "complex multiplier" is the most generic means for applying a complex adjustment factor $\rho$ to one or more complex beam signal samples. If the polar format representation for $\rho$ is used, then separate steps using a single "real multiplication" by the amplitude factor "a" and using a "phase rotation" by a phase factor $\theta$ are the appropriate enabling means. If the in-phase and quadrature format representation for $\rho$ is used, then separate "real multiplications" by the two factors $a \cdot \cos\theta$ and $a \cdot \sin\theta$ are the appropriate means, in which case the $\theta$ factor is represented as a "phase shift" operation. Describing a "complex multiplier" here includes those arrangements involving or using real multipliers, phase rotators, and phase shifters.

The three term product of the phasor $\rho(r_t)$ has a geometric term $G_\rho$, an apodization term $A_\rho$, and an origin term $O_\rho$. $G_\rho$ is dominated by dependencies on the transducer array and scan geometry and includes broadband pulse effects. Observe that for targets at increasing ranges from the transmit/receive scan line axis, term $(1+\sigma^2\beta^2)$ increases so that the two-way Gaussian pulse bandwidth and center frequency decreases due to the lowpass filtering effect of temporal dispersion. The term $A_\rho$ is dominated by dependencies on the apodization which is assumed to have Gaussian shape. The origin term $O_\rho$ is simply the product of the transmit and receive origin terms $O_x$ and $O_r$ and contains the beam loss and an additional phase shift term imposed on the beam due to its transmit/receive apodization origins $x_{ax}$ and $x_{ar}$ being displaced from the transmit/receive scan line origins $x_{ox}$ and $x_{or}$ respectively. $O_{92}$ also accounts for the effective apodization shifting due to element factor and attenuation effects.

Denoting the relative phasor response at range $r_t$ along scan line 1 as $\rho_1(r_t) = A_1 e^{j\psi_1}$ and along scan line 2 as $\rho_2(r_t) = A_2 e^{j\psi_2}$, where $A_1$ and $A_2$ are the relative amplitude responses and where $\psi_1$ and $\psi_2$ are the relative phase responses, the amplitude difference that requires amplitude adjustment of one or both scan line responses at range $r_t$ in order to match amplitude response involves the gain factor $A_2/A_1$ (or $A_1/A_2$), and the phase difference that requires phase adjustment of one or both scan line responses at range $r_t$ is the factor $\psi_1-\psi_2$ (or $\psi_2-\psi_1$). There is one scan format that basically requires no amplitude or phase adjustments in order to maintain amplitude and phase coherence for purposes, as an example, of interpolating new scan line samples. Consider a sector scan format of a linear array in which the scan vertex is located at the center of the array. Also assume that the same imaging center frequency is used to produce all scan lines and a symmetric apodization is applied. In this case, $x_{ox} = x_{or} = x_t = x_{ax} = x_{ar}$ and the various difference expressions, such as $x_{tox} = x_t - x_{ox}$, are all zero. In this situation, the equation in Table 1 yields phase terms (having the form $e^{j\psi}$ for some phase argument $\psi$) which are essentially zero, and amplitude terms for a given range that are identical for all scan lines. Thus, the sector scan format generally requires no amplitude or phase adjustments as there is already nearly full coherence among scan lines at a given range.

Although the phasor equation of Table 1 provides an analytical expression for a systematic understanding of amplitude and phase adjustments needed to maintain inter-scan-line coherence, evaluating such an expression as part of a real-time scanning operation would be prohibitive. An alternative approach amenable to real-time implementation is to precalculate amplitude and phase correction values evaluated on a sparse grid of reference ranges indexed by scan line number. Interpolation into the sparse grid of amplitude and phase correction values for arbitrary range and/or arbitrary scan lines between indexed scan lines can then produce approximate amplitude and phase corrections that are applied by the complex multiplier B-246, or comparable apparatus such as real multiplier for amplitude and phase rotator for phase, to each sample of each scan line.

Consider a specific case of generating the phase adjustment. The phase portion of the correction is simply the difference of the individual scan line relative phase responses.

$$\psi_2(r_t) - \psi_1(r_t) = -\Delta\phi(r_t)$$

Figure 9:
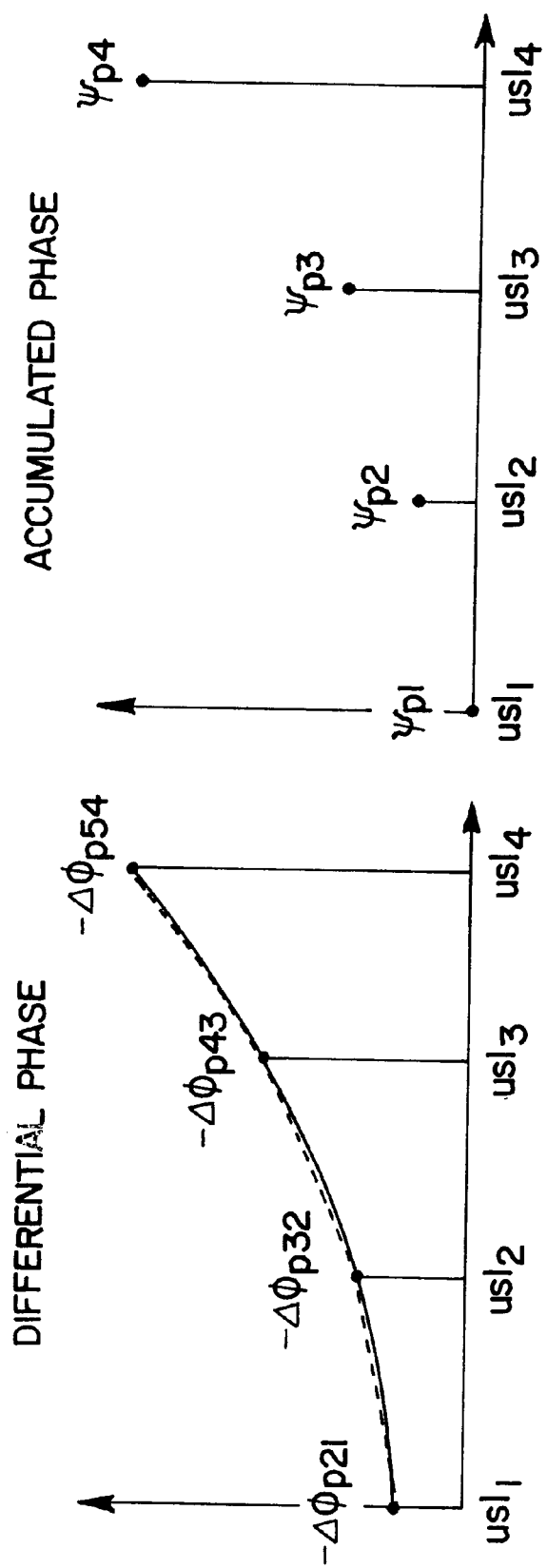
FIG. 9 demonstrates a plot (left) of the differential phase for a sequence of acquired ultrasonic scan lines (usl) and a plot (right) of the accumulated (integrated) phase.

Although the phase difference $\Delta\phi$ can be computed across scan lines, it does not determine the individual scan line phases $\psi_1$ and $\psi_2$ needed to phase correct or phase align the individual scan line samples. Consider FIG. 8 which shows the phase differences for a group of scan lines spaced at a nominal scan line spacing, where the dashed lines indicate target scan lines. The phase $\psi$ for a given phase correction reference scan line, which for single beam scanning modes is set equal to the target scan line, is determined such that the phase differences formed from neighboring $\psi$ result in either using $-\Delta\phi$ directly, or is the result of a linear interpolation of neighboring phase differences. Starting from the center scan line and scanning to the right in FIG. 8, the phases are accumulated in the following manner. The phase $\psi_1$ is set to zero since the absolute phase reference is completely arbitrary; $\psi_2 = -\frac{1}{2} \cdot (\Delta\phi_{21} + \Delta\phi_{32})$, $\psi_3 = \psi_2 - \frac{1}{2} \cdot (\Delta\phi_{32} + \Delta\phi_{43})$, etc. This is simply numerical integration of the differential phases across reference scan lines, which in this discussion employs the trapezoidal rule. Trapezoidal integration approximates the integral of a function by accumulating the areas of trapezoids. This is shown in FIG. 9 where the dashed line indicate the trapezoidal approximation to the continuous differential phase correction values indicated by the solid line. The resulting trapezoidal integration is given mathematically by $$\psi_1 = 0$$

$$\psi_2 = \psi_1 - \frac{1}{2}(\Delta\phi_{21} + \Delta\phi_{32}) = -\frac{1}{2}(\Delta\phi_{21} + \Delta\phi_{32})$$

$$\psi_3 = \psi_2 - \frac{1}{2}(\Delta\phi_{32} + \Delta\phi_{43}) = -\frac{1}{2}(\Delta\phi_{21} + 2\Delta\phi_{32} + \Delta\phi_{43})$$

$$\psi_4 = \psi_3 - \frac{1}{2}(\Delta\phi_{43} + \Delta\phi_{54}) = -\frac{1}{2}(\Delta\phi_{21} + 2\Delta\phi_{32} + 2\Delta\phi_{43} + \Delta\phi_{54})$$

and so forth.

During real-time B-mode imaging, the baseband processor will apply the range-varying accumulated phase correction values to each range sample of each receive scan line. If a given range sample does not coincide with a phase correction value in the precalculated table at a reference scan line and a reference range, the baseband processor control linearly interpolates among the accumulated phase correction values in scan line and range to produce a correction phase. Practical consideration of memory size will limit the number of reference ranges and reference scan lines, so it is desirable to distribute the reference points in the range-scan-line grid in a manner which minimizes the phase error between desired phase correction values and interpolated phase correction values over the image region. The differential phase varies most rapidly near the transmit focus. Since the phase accumulation occurs across scan lines, the phase correction values will also vary most rapidly near the transmit focus. Therefore, it is advantageous to place a higher density of reference ranges near the transmit focus to accurately track phase variations in range by the piecewise linear approximation approach which has been described, and a lower density of reference ranges in regions which exhibit phase variations which vary slowly with range. The distribution of reference scan lines will therefore use non-uniform spacing, with the highest concentration of reference ranges where the phase changes rapidly.

TABLE 1

$$\rho(r_t) = G_\rho \cdot A_\rho \cdot O_\rho$$

$$\rho(r_t) = \underbrace{G_0 e^{-\pi\frac{\sigma^2(2r_t - R_{to})^2}{c^2(1+\sigma^2\beta^2)}} e^{\frac{2\pi j f_c(r_t)(2r_t - R_{to})}{c(1+\sigma^2\beta^2)}}}_{G_\rho} \underbrace{\left[\frac{W_{iix}}{\alpha_x(\lambda_c)}\right]\left[\frac{W_{iir}}{\alpha_r(\lambda_c)}\right]\frac{e^{-\pi\frac{\beta^2 f_c^2(r_t)}{(1+\sigma^2\beta^2)}}}{\sqrt{1+\sigma^2\beta^2}}}_{A_\rho} \underbrace{O_x(\lambda_c)O_r(\lambda_c)}_{O_\rho}$$

$$f_c(r_t) = \frac{\sigma^2}{\sigma_{sys}^2}\left[f_{c0} - \frac{\gamma}{2\pi}\sigma_{sys}^2(R_{tax} + R_{tar})\right] + \frac{\sigma^2}{\sigma_{BBF}^2}f_d(r_t) \quad \lambda_c(r_t) = \frac{c}{f_c(r_t)} \quad \sigma = \frac{\sigma_{sys}\sigma_{BBF}}{\sqrt{\sigma_{sys}^2 + \sigma_{BBF}^2}}$$

$$R_{to} = R_{tox} + R_{tor} = 2r_t + \sin\theta_{t\perp}(x_{tox} + x_{tor}) + \frac{1}{2}\left(\frac{\cos^2\theta_{t\perp}}{r_t} + \frac{\cos\theta_{t\perp}}{R_{xdcr}}\right)(x_{tox}^2 + x_{tor}^2)$$

$$R_{tax} = \sqrt{r_t^2 - 2r_t\sin\theta_{t\perp}x_{atx} + \left(1 + \frac{r_t}{R_{xdcr}}\cos\theta_{t\perp}\right)x_{atx}^2}$$

$$R_{tar} = \sqrt{r_t^2 - 2r_t\sin\theta_{t\perp}x_{atr} + \left(1 + \frac{r_t}{R_{xdcr}}\cos\theta_{t\perp}\right)x_{atr}^2}$$

$$\beta^2 = \beta_x^2(\lambda_c) + \beta_{ex}^2 + \beta_r^2(\lambda_c) + \beta_{er}^2 \quad G_0 = \frac{e^{\pi\left[\frac{f_c^2(r_t)}{\sigma^2} - \frac{f_{c0}^2}{\sigma_{sys}^2} - \frac{f_d^2(r_t)}{\sigma_{BBF}^2}\right]}}{16\pi^2 R_{tax}R_{tar}\sqrt{\sigma_{sys}^2 + \sigma_{BBF}^2}}$$

$$\beta_x^2(\lambda_c) = \frac{W_{iix}^2 s_x^2}{\alpha_x^2(\lambda_c)c^2} \quad s_x = (\sin\theta_{t\perp} - \sin\theta_{x\perp}) + \left(\frac{\cos^2\theta_{t\perp}}{r_t} + \frac{\cos\theta_{t\perp}}{R_{xdcr}}\right)x_{tox}$$

$$\beta_r^2(\lambda_c) = \frac{W_{iir}^2 s_r^2}{\alpha_r^2(\lambda_c)c^2} \quad s_r = (\sin\theta_{t\perp} - \sin\theta_{r\perp}) + \left(\frac{\cos^2\theta_{t\perp}}{r_t} + \frac{\cos\theta_{t\perp}}{R_{xdcr}}\right)x_{tor}$$

$$\beta_{ex}^2 = \frac{W_e^2 \sin^2\theta_{eax}}{c^2} \quad \sin\theta_{eax} = \frac{\left[r_t\sin\theta_{t\perp} - \left(1 + \frac{r_t}{R_{xdcr}}\cos\theta_{t\perp}\right)x_{atx}\right]}{R_{tax}}$$

$$\beta_{er}^2 = \frac{W_e^2 \sin^2\theta_{ear}}{c^2} \quad \sin\theta_{ear} = \frac{\left[r_t\sin\theta_{t\perp} - \left(1 + \frac{r_t}{R_{xdcr}}\cos\theta_{t\perp}\right)x_{atr}\right]}{R_{tar}}$$

$$\alpha_x^2(\lambda_c) = \left\{1 + j\frac{W_{iix}^2}{\lambda_c}\left[\left(\frac{\cos^2\theta_{t\perp}}{r_t} + \frac{\cos\theta_{t\perp}}{R_{xdcr}}\right) - \left(\frac{\cos^2\theta_{x\perp}}{r_x} + \frac{\cos\theta_{x\perp}}{R_{xdcr}}\right)\right]\right\}$$

TABLE 1-continued $$\alpha_r^2(\lambda_c) = \left\{1 + j\frac{W_{\|r}^2}{\lambda_c}\left[\left(\frac{\cos^2\theta_{t\perp}}{r_t} + \frac{\cos\theta_{t\perp}}{R_{xdcr}}\right) - \left(\frac{\cos^2\theta_{r\perp}}{r_r} + \frac{\cos\theta_{r\perp}}{R_{xdcr}}\right)\right]\right\}$$

$$O_x(\lambda_c) = E_{0x}F_{0x}\, e^{\frac{2\pi j s_x x_{\|ox}}{\lambda_c \alpha_x^2(\lambda_c)}}\, e^{-\pi\frac{\left[1-\frac{1}{\alpha_x^2(\lambda_c)}\right]x_{\|ox}^2}{W_{\|x}^2}} \qquad O_r(\lambda_c) = E_{0r}F_{0r}\, e^{\frac{2\pi j s_r x_{\|or}}{\lambda_c \alpha_r^2(\lambda_c)}}\, e^{-\pi\frac{\left[1-\frac{1}{\alpha_r^2(\lambda_c)}\right]x_{\|or}^2}{W_{\|r}^2}}$$

$$E_{0x} = W_e\cos\theta_{eax}\,\text{sinc}\left(\frac{W_e\sin\theta_{eax}}{\lambda_c}\right)e^{-\pi\frac{W_e^2\sin^2\theta_{eax}}{\lambda_c^2}}\, e^{-\pi\frac{(x_{aox}-x_{efox})^2}{W_{efx}^2}}$$

$$E_{0r} = W_e\cos\theta_{ear}\,\text{sinc}\left(\frac{W_e\sin\theta_{ear}}{\lambda_c}\right)e^{-\pi\frac{W_e^2\sin^2\theta_{ear}}{\lambda_c^2}}\, e^{-\pi\frac{(x_{aor}-x_{efor})^2}{W_{efr}^2}}$$

$$\cos\theta_{eax} = \frac{r_t\cos\theta_{t\perp} + \frac{r_t}{R_{xdcr}}\sin\theta_{t\perp}x_{atx} - \frac{1}{2}\left(1+\frac{r_t}{R_{xdcr}}\cos\theta_{t\perp}\right)\frac{x_{atx}^2}{R_{xdcr}}}{R_{tax}}$$

$$\cos\theta_{ear} = \frac{r_t\cos\theta_{t\perp} + \frac{r_t}{R_{xdcr}}\sin\theta_{t\perp}x_{atr} - \frac{1}{2}\left(1+\frac{r_t}{R_{xdcr}}\cos\theta_{t\perp}\right)\frac{x_{atr}^2}{R_{xdcr}}}{R_{tar}}$$

$$F_{0x} = e^{\pi\frac{(x_{aox}-x_{\gamma ox})^2}{W_{\gamma x}^2}}\, e^{\pi\frac{x_{\|ox}^2}{W_{\|x}^2}}\, e^{-\pi\left(\frac{x_{aox}^2}{W_x^2} + \frac{x_{efox}^2}{W_{efx}^2} + \frac{x_{\gamma ox}^2}{W_{\gamma x}^2}\right)}$$

$$F_{0r} = e^{\pi\frac{(x_{aor}-x_{\gamma or})^2}{W_{\gamma r}^2}}\, e^{\pi\frac{x_{\|or}^2}{W_{\|r}^2}}\, e^{-\pi\left(\frac{x_{aor}^2}{W_r^2} + \frac{x_{efor}^2}{W_{efr}^2} + \frac{x_{\gamma or}^2}{W_{\gamma r}^2}\right)}$$

$$x_{\|ox} = W_{\|x}^2\left(\frac{x_{aox}}{W_x^2} + \frac{x_{efox}}{W_{efx}^2} + \frac{x_{\gamma ox}}{W_{\gamma x}^2}\right) \qquad W_{\|x} = \frac{1}{\sqrt{\frac{1}{W_x^2} + \frac{1}{W_{efx}^2} + \frac{1}{W_{\gamma x}^2}}}$$

$$x_{\|or} = W_{\|r}^2\left(\frac{x_{aor}}{W_r^2} + \frac{x_{efor}}{W_{efr}^2} + \frac{x_{\gamma or}}{W_{\gamma r}^2}\right) \qquad W_{\|r} = \frac{1}{\sqrt{\frac{1}{W_r^2} + \frac{1}{W_{efr}^2} + \frac{1}{W_{\gamma r}^2}}}$$

$$x_{efox} = x_{tox} + \frac{r_t\sin\theta_{t\perp}}{\left(1+\frac{r_t}{R_{xdcr}}\cos\theta_{t\perp}\right)} \qquad W_{efx} = \frac{\lambda_c R_{tax}}{W_e\left(1+\frac{r_t}{R_{xdcr}}\cos\theta_{t\perp}\right)}$$

$$x_{efor} = x_{tor} + \frac{r_t\sin\theta_{t\perp}}{\left(1+\frac{r_t}{R_{xdcr}}\cos\theta_{t\perp}\right)} \qquad W_{efr} = \frac{\lambda_c R_{tar}}{W_e\left(1+\frac{r_t}{R_{xdcr}}\cos\theta_{t\perp}\right)}$$

$$x_{\gamma ox} = x_{aox} + \frac{R_{tax}^2\left[r_t\sin\theta_{t\perp} - \left(1+\frac{r_t}{R_{xdcr}}\cos\theta_{t\perp}\right)x_{atx}\right]}{r_t^2\left(\cos^2\theta_{t\perp} + \frac{r_t}{R_{xdcr}}\cos\theta_{t\perp}\right)}$$

$$W_{\gamma x} = \sqrt{\frac{2\pi R_{tax}^3}{\gamma f_c r_t^2\left(\cos^2\theta_{t\perp} + \frac{r_t}{R_{xdcr}}\cos\theta_{t\perp}\right)}}$$

$$x_{\gamma or} = x_{aor} + \frac{R_{tar}^2\left[r_t\sin\theta_{t\perp} - \left(1+\frac{r_t}{R_{xdcr}}\cos\theta_{t\perp}\right)x_{atr}\right]}{r_t^2\left(\cos^2\theta_{t\perp} + \frac{r_t}{R_{xdcr}}\cos\theta_{t\perp}\right)}$$

TABLE 1-continued $$W_{\gamma r} = \sqrt{\frac{2\pi R_{tar}^3}{\gamma f_c r_t^2 \left(\cos^2 \theta_{t\perp} + \frac{r_t}{R_{xdcr}} \cos \theta_{t\perp}\right)}}$$

$$x_{ax} = \frac{\int_{-\infty}^{\infty} a_x(x)x\,dx}{W_x} \approx \frac{d \cdot \sum_{n=0}^{N-1} a_x(x_n)x_n}{W_x} \quad W_x = \int_{-\infty}^{\infty} a_x(x)\,dx \approx d \cdot \sum_{n=0}^{N-1} a_x(x_n)$$

$$x_{ar} = \frac{\int_{-\infty}^{\infty} a_r(x)x\,dx}{W_r} \approx \frac{d \cdot \sum_{n=0}^{N-1} a_r(x_n)x_n}{W_r} \quad W_r = \int_{-\infty}^{\infty} a_r(x)\,dx \approx d \cdot \sum_{n=0}^{N-1} a_r(x_n)$$

$x_{tox} = x_t - x_{ox}$     $x_{aox} = x_{ax} - x_{ox}$     $x_{atx} = x_{ax} - x_t$
$x_{tor} = x_t - x_{or}$     $x_{aor} = x_{ar} - x_{or}$     $x_{atr} = x_{ar} - x_t$
$f_c(r_t)$ = effective imaging center frequency     $f_{c0}$ = imaging center frequency (zero depth)
$f_d(r_t)$ = demodulation frequency     $\psi_d(r_t)$ = demodulation phase     $\gamma$ = attenuation
$r_x$ = transmit focus range     $r_r$ = receive focus range     $r_t$ = target range
$\theta_{x\perp}$ = transmit usl angle     $\theta_{r\perp}$ = receive usl angle     $\theta_{t\perp}$ = target usl angle
$x_{ox}$ = transmit usl origin     $x_{or}$ = receive usl origin     $x_t$ = target usl origin
$x_{ax}$ = transmit gaussian apodization origin     $x_{ar}$ = receive gaussian apodization origin
$W_x$ = transmit gaussian apodization width     $W_r$ = receive gaussian apodization width
d = element spacing     $W_e$ = element width     $R_{xdcr}$ = transducer radius     N = # of elements Note: Angles are with respect to the array surface normal and c is the acoustic propagation velocity.

We claim:

1. An ultrasound receive beamformer system comprising:
   (a) a receive beamformer adapted to acquire a plurality of beamformed baseband samples on at least one receive scan line; and
   (b) a complex response adjuster adapted to operate on said samples to effect coherence between samples.

2. The beamformer system of claim 1 wherein the complex response adjuster comprises a phase adjuster, said phase adjuster operating on said beamformed samples to effect phase coherence between said samples, thereby creating phase coherent samples.

3. The beamformer system of claim 2 wherein the complex response adjuster further comprises an amplitude adjuster which operates on the beamformed samples to effect amplitude coherence between said samples, thereby creating amplitude coherent samples.

4. The beamformer system of claim 3 wherein the amplitude adjuster comprises a real-value multiplier.

5. The beamformer system of claim 2 wherein:
   said phase adjuster operates on the phase of the beamformed samples to effect phase coherence between samples on different scan lines.

6. The beamformer system of claim 2 wherein:
   said phase adjuster operates on the beamformed samples to effect phase coherence between samples on the same scan line.

7. The beamformer system of claim 2 wherein:
   said phase adjuster remodulates the beamformed samples on at least one receive scan line.

8. The beamformer system of claim 7 wherein said phase adjuster remodulates the beamformed samples on distinct receive scan lines associated with distinct beams using different frequencies to effect beam-to-beam coherence.

9. The beamformer system of claim 2 wherein the phase adjuster comprises a phase rotator.

10. The beamformer system of claim 2 wherein the phase adjuster comprises a complex value multiplier.

11. The beamformer system of claim 1 comprising a baseband processor, wherein said baseband processor includes said complex response adjuster.

12. The beamformer system of claim 11 wherein the baseband processor further comprises a baseband filter for filtering said samples.

13. The beamformer system of claim 12 wherein the baseband filter is connected to receive as input said beamformed samples and wherein said complex response adjuster is connected to receive the output of the baseband filter.

14. The beamformer system of claim 12 wherein the complex response adjuster is connected to receive as input said beamformed samples and said baseband filter is connected to receive the output of said complex response adjuster.

15. The beamformer system of claim 12 wherein the baseband filter comprises a programmable filter.

16. The beamformer system of claims 12 or 15 wherein the baseband filter comprises a sample rate converter.

17. The beamformer system of claim 12 wherein:
   said baseband filter is adapted to increase the signal-to-noise ratio of said beamformed samples from said beamformer by rejecting out-of-band noise frequencies.

18. The beamformer system of claim 12 wherein said baseband filter is adapted to shape said beamformed samples from said beamformer.

19. The beamformer system of claim 12 wherein said baseband filter is adapted to effect a match-filtered response to said beamformed samples.

20. The beamformer system of claim 12 wherein:
   said baseband filter is adapted to produce an approximately Gaussian-shaped response to said beamformed samples.

21. The beamformer system of claims 1 or 12 wherein the complex response adjuster comprises:
   (a) a phase adjuster adapted to create phase coherent samples; and
   (b) an amplitude adjuster adapted to create amplitude coherent samples.

22. The beamformer system of claim 21 wherein the amplitude adjuster comprises a real-value multiplier.

23. The beamformer system of claims 1 or 12 wherein the complex response adjuster comprises a complex-value multiplier.

24. The beamformer system of claims 11, 12, or 15, wherein the baseband processor further comprises a sample rate converter.

25. The beamformer system of claim 12 wherein said baseband filter compensates for at least one of transducer frequency response and analog signal path response.

26. An ultrasound receive beamformer comprising:
(a) a plurality of receive processors forming a plurality of receive baseband samples;
(b) a plurality of complex response adjusters operating on said plurality of receive baseband samples to produce adjusted baseband samples; and
(c) a summer for summing said adjusted baseband samples to form a plurality of receive beam signals;
wherein said complex response adjusters effect beam-to-beam coherence between said receive beam signals.

27. The receive beamformer of claim 26 wherein:
each of said complex response adjusters is further adapted to perform complex demodulation.

28. The receive beamformer of claim 26 further comprising:
a baseband filter to receive the receive beam signals from the summer.

29. An ultrasound receive beamformer system comprising:
(a) a beamformer that generates time-interleaved baseband beamformed samples representative of a plurality of receive scan lines; and
(b) a baseband processor for processing said beamformed samples, comprising a baseband filter adapted to operate on said time-interleaved samples to produce time-interleaved filtered samples.

30. The beamformer system of claim 29 wherein the baseband processor further comprises a complex response adjuster operating on said time-interleaved beamformed samples or said time-interleaved filtered samples to effect coherence between samples.

31. A method for processing baseband signals from an ultrasound beamformer comprising:
(a) acquiring a plurality of beamformed baseband samples from an ultrasound beamformer, said plurality of beamformed baseband samples acquired on at least one receive scan line; and
(b) adjusting the complex response between said beamformed baseband samples to effect coherence between samples.

32. The method of claim 31 wherein the step of adjusting the complex response comprises adjusting the phase of said beamformed baseband samples to effect phase coherence between said samples, thereby creating phase coherent samples.

33. The method of claim 32 wherein the step of adjusting the complex response further comprises adjusting the amplitude of the beamformed samples to effect amplitude coherence between said samples, thereby creating amplitude coherent samples.

34. The method of claim 33 wherein the step of adjusting the amplitude comprises using a real-value multiplier.

35. The method of claim 32 wherein:
the step of adjusting the phase of said beamformed samples comprises adjusting the phase of the beamformed samples to effect phase coherence between samples on different scan lines.

36. The method of claim 32 wherein:
the step of adjusting the phase of said beamformed samples comprises adjusting the beamformed samples to effect phase coherence between samples on the same scan line.

37. The method of claim 32 wherein:
the step of adjusting the phase of said beamformed samples comprises remodulating the beamformed samples on at least one receive scan line.

38. The method of claim 37 wherein said beamformed samples are acquired on distinct scan lines associated with receive beams using different frequencies, and the step of remodulating comprises remodulating the samples to effect coherence between samples on said distinct scan lines.

39. The method of claim 32 wherein the step of adjusting the phase comprises rotating the phase.

40. The method of claim 32 wherein the step of adjusting the phase comprises complex multiplication.

41. The method of claim 31 further comprising filtering at baseband.

42. The method of claim 41 wherein the filtering step is performed prior to the adjusting step.

43. The method of claim 41 wherein the adjusting step is performed prior to the filtering step.

44. The method of claim 41 wherein the step of adjusting the complex response comprises using a complex response adjuster and the step of filtering at baseband comprises using a programmable filter.

45. The method of claims 41 or 44 further comprising converting the sample rate.

46. The method of claim 41 comprising:
increasing the signal-to-noise ratio of said beamformed samples from said ultrasound beamformer by rejecting out-of-band noise frequencies using said baseband filter.

47. The method of claim 41 comprising shaping said beamformed samples from said ultrasound beamformer using said baseband filter.

48. The method of claim 41 comprising effecting a match-filtered response to said beamformed samples using said baseband filter.

49. The method of claim 41 comprising:
producing an approximately Gaussian-shaped response to said beamformed samples using said baseband filter.

50. The method of claims 31 or 41 wherein the step of adjusting complex response comprises:
(a) adjusting the phase of said beamformed samples to create phase coherent samples; and
(b) adjusting the amplitude of said samples to create amplitude coherent samples.

51. The method of claim 50 wherein the step of adjusting the amplitude comprises using a real-value multiplier.

52. The method of claims 31 or 41 wherein the step of adjusting complex response comprises using a complex-value multiplier.

53. The method of claims 31, 41, or 44 further comprising using a sample rate converter.

54. The method of claim 41 comprising compensating for at least one of transducer frequency response and analog signal path response.

55. A method for ultrasound receive beamformation comprising:
(a) forming a plurality of receive baseband samples using a plurality of receive processors;
(b) operating on said plurality of receive baseband samples to produce adjusted baseband samples; and (c) summing said adjusted baseband samples to form a plurality of receive beam signals;

wherein said operating step effects beam-to-beam coherence between said receive beam signals.

56. The method of claim 55 wherein:

the step of operating on said plurality of baseband samples further comprises using a complex demodulator.

57. The method of claim 58 further comprising:

using a baseband filter to receive the receive beam signals from the summer.

58. A method for processing baseband signals comprising:

(a) generating time-interleaved baseband beamformed samples from an ultrasound beamformer, said time-interleaved baseband beamformed samples representative of a plurality of receive scan lines; and (b) filtering said time-interleaved samples to produce time-interleaved filtered samples.

59. The method of claim 58 further comprising operating on said time-interleaved beamformed samples or said time-interleaved filtered samples to effect coherence between samples.

* * * * *

UNITED STATES PATENT AND TRADEMARK OFFICE
CERTIFICATE OF CORRECTION

PATENT NO. : 5,928,152
DATED : July 27, 1999
INVENTOR(S) : J. Nelson Wright et al.

It is certified that error appears in the above-identified patent and that said Letters Patent is hereby corrected as shown below:

In columns 23-24, equation 13, change "$x_{yor}$" to --$x_{yox}$--.

<u>In the Claims</u>

In claim 57, line 1, change "58" to --55--.

Signed and Sealed this

Sixteenth Day of May, 2000

Attest:

Q. TODD DICKINSON

*Attesting Officer*      *Director of Patents and Trademarks*